United States Patent
Ishikawa

(10) Patent No.: US 9,234,247 B2
(45) Date of Patent: Jan. 12, 2016

(54) METHOD FOR DETECTION OF MUTANT GENE

(75) Inventor: Tomokazu Ishikawa, Amagasaki (JP)

(73) Assignee: Wako Pure Chemical Industries, Ltd., Osaka (JP)

(*) Notice: Subject to any disclaimer, the term of this patent is extended or adjusted under 35 U.S.C. 154(b) by 1461 days.

(21) Appl. No.: 12/282,339

(22) PCT Filed: Mar. 12, 2007

(86) PCT No.: PCT/JP2007/054785
§ 371 (c)(1),
(2), (4) Date: Sep. 9, 2008

(87) PCT Pub. No.: WO2007/105673
PCT Pub. Date: Sep. 20, 2007

(65) Prior Publication Data
US 2009/0053729 A1    Feb. 26, 2009

(30) Foreign Application Priority Data

Mar. 13, 2006 (JP) ................. 2006-067495

(51) Int. Cl.
*C12Q 1/68* (2006.01)
(52) U.S. Cl.
CPC .............. *C12Q 1/689* (2013.01); *C12Q 1/6827* (2013.01)
(58) Field of Classification Search
None
See application file for complete search history.

(56) References Cited

U.S. PATENT DOCUMENTS

| | | | |
|---|---|---|---|
| 6,316,198 B1 * | 11/2001 | Skouv et al. | 435/6.12 |
| 2003/0148301 A1 | 8/2003 | Aono et al. | |
| 2007/0009897 A1 * | 1/2007 | Koizumi | 435/6 |

FOREIGN PATENT DOCUMENTS

| | | |
|---|---|---|
| EP | 1 688 493 A1 | 8/2006 |
| JP | 1993-271224 A | 10/1993 |
| JP | 2005-323583 A | 11/2005 |
| WO | WO 95/33851 A2 | 12/1995 |
| WO | WO 2005/045033 A1 | 5/2005 |

OTHER PUBLICATIONS

Di Giusto et al. (Nucleic Acids Research, 2004, 32(3):e32, p. 1-8).*
LaTorra et al. (Human Mutation, 2003, 22:79-85).*
Koizumi et al. (Nucleic Acids Research, 2003, 31(12):3267-3273).*
Johnson et al. (Nucleic Acids Research, 2004, 32(6):e55, p. 1-9).*
Gale et al. (Photochemistry and Photobiology, 2004, 79(5):461-469).*
Kapur et al., *Journal of Clinical Microbiology*, 32(4): 1095-1098 (Apr. 1994).
Morita et al., *Bioorganic and Medicinal Chemistry Letters*, 12: 73-76 (2002).
Morita et al., *Bioorganic and Medicinal Chemistry*, 11: 2211-2226 (2003).
European Patent Office, Extended European Search Report in European Patent Application No. 07 73 8257 (Mar. 2, 2010).
Japanese Patent Office, International Search Report in International Patent Application No. PCT/JP2007/054785 (Jun. 12, 2007).
Japanese Patent Office, International Preliminary Report on Patentability in International Patent Application No. PCT/JP2007/054785 (Sep. 16, 2008).

* cited by examiner

*Primary Examiner* — Stephanie K Mummert
(74) *Attorney, Agent, or Firm* — Leydig, Voit & Mayer, Ltd.

(57) ABSTRACT

Disclosed is a method for detecting mutation(s) in nucleotide sequence, which comprises performing a nucleic acid amplification reaction by using an oligonucleotide or a salt thereof as a primer and a nucleic acid in a sample as a template and detecting a reaction product, wherein the oligonucleotide is so modified at the nucleotide at the second position from the 3'-terminus as to inhibit the nucleic acid synthesis. Also disclosed is a kit for the method. According to the present invention, since it is possible to completely eliminate any false positive result in the determination and correspond to various mutation patterns by a single run of PCR1 reaction, it becomes possible to design a drug-resistance determination system, which can detect possible plural genetic mutations by a single run of multiplex PCR.

12 Claims, 6 Drawing Sheets

METHOD FOR DETECTION OF MUTANT GENE

INCORPORATION-BY-REFERENCE OF MATERIAL ELECTRONICALLY SUBMITTED

Incoporated by reference in its entirety herein is a computer-readable nucleotide/amino acid sequence listing submitted concurrently herewith and identified as follows: 2,763 bytes ASCII (Text) file named "SequenceListing-703438.txt," created Sep. 9,2008.

TECHNICAL FIELD

The present invention relates to a specific method for detecting mutation(s) in nucleotide sequence and a kit to be used therefor.

BACKGROUND ART

In case of human, for example, one of the reasons for difference between individual subjects in susceptibility to diseases, reactivity to medical drugs, susceptibility to side effect and the like may be due to the involvement of a genetic mutation (base polymorphism of gene). And so, focusing attention on this difference of nucleotide sequence, studies on the exploration of a suitable therapy for the individual constitution have been progressing. In addition, the base polymorphism of gene can also be genetic markers for various diseases. Therefore, the clarification of such base polymorphism is important from the clinical point of view, and the establishment of a method for analyzing nucleotide sequence which is capable of detecting the respective mutant gene and a method for identifying such base polymorphism has long been desired.

In addition, in the field of diagnosis of infectious diseases, there is an occasion where the infecting microorganism has developed resistance to drug by a genetic mutation. Therefore, for the purpose of determining whether the microorganism isolated from the patient has developed resistance to the medical agent, the detection of a genetic mutation in the microorganism isolated from the patient is particularly important from a viewpoint of diagnostic methodology and also for the selection of appropriate therapeutic treatment.

For example, it has been clarified that a mutation of rpoB gene coding for RNA polymerase B subunit of genus *Mycobacterium* is involved in development of resistance to rifampicin in human tubercle bacillus (*Mycobacterium tuberculosis*), and the mutation in rpoB gene was observed for about 95% of the rifampicin-resistant tubercle bacilli. And so, it may be possible to figure out whether the tubercle bacillus is resistant to rifampicin or not by detecting this gene and by determining the existence or non-existence of genetic mutation.

In addition, as to the mutation in rpoB gene involved in the rifampicin resistance of tubercle bacillus, various patterns have been reported (VIVEK KAPUR, et al., J. Clin. Microbiol. 1944. p. 1095-1098). Therefore, if the detection of plural number of mutant genes can be performed at the same time, improved accuracy in the diagnosis and increased throughput (the amount of information processed in a certain period) can be expected.

As to the tubercle bacillus, the genetic mutation involved in the resistance to other medical drugs has also been studied, and it is now coming to light the patterns for the respective mutations.

Another example showing effectiveness of the detection of mutation is the detection of MRSA. That is, as the methicillin-resistant *Streptococcus aureus* (MRSA) has mec gene, the resistance to methicillin can be recognized by the detection of the mec gene (MRSA can be detected).

However, in order to detect the existence of mutant gene such as a point mutation, a single nucleotide polymorphism, and the like, difference of only one base in a huge genomic nucleotide sequence has to be detected, and in consequence, a very high specificity is required.

Examples of known analytical technique of the nucleotide sequence which is conventionally and commonly used are, for example, the determination method of nucleotide sequence determination (sequencing method), TaqMan™ probe method (Genome Res., vol. 6, p. 986, 1996), RFLP (restriction fragment length polymorphism) method (J. Clin. Invest., vol. 72, p. 1262, 1983), ASP (allele-specific primer) method (WO 01/42498), ASO (allele-specific oligoprobe) method (Nature, vol. 324, p. 163, 1986), Single base extension method (Proc. Natl. Acad. Sci. USA, vol. 94, p. 10756, 1997), Pyrosequencing method (Analytical Biochemistry, vol. 244, p. 367, 1997), Invader™ method (Nature Biotech., vol. 17, p. 292, 1999), and so on.

Among these methods, the method of nucleotide sequence determination, TaqMan™ probe method, RFLP method, ASO method, Single base extension method, Pyrosequencing method and the like are the methods in which a region comprising a mutation or a polymorphism is amplified in advance using nucleic acid amplification technique such as Polymerase Chain Reaction (PCR), then the detection procedure is performed. Therefore, in order to obtain a clear signal with reduced background, to obtain a specific amplification product is primarily quite important.

Invader™ method is an accepted method in principle, which can detect the mutation and polymorphism without any amplification reaction. However, there are many cases where the sensitivity is insufficient for the detection when the method is practiced without amplification reaction. Practically, same as the case with other methods, it is important to amplify the nucleotide of the measuring object to be detected in advance.

Further, in the ASP method, after amplifying the mutant allele specifically by PCR using a mutant DNA-specific oligonucleotide comprised of about 20 bases and a template DNA, the PCR product obtained is subjected to gel electrophoresis, and the existence of a mutant allele is detected by detecting a band. This method is eventually suitable for testing a large number of samples efficiently.

However, in the conventional methods using PCR as described above including the ASP method, there are some cases where a primer extension product is obtained even when mismatches exist in the primer, and so that there exists difficulty in obtaining a specific amplification product. Therefore, the method is problematic in terms of stringency.

In addition, there is a method which uses a primer having a nucleoside with a base which is not complementary to a target gene at the second position from 3'end, and setting the polymorphic site to be detected at the 3'end thereof, incidentally the method has been modified from the ASP method based on the knowledge that the polymorphism-specific primer having SNP site at the second position from the 3' end thereof recognizes the polymorphism precisely. There is a publication reporting that, in this method, detection of the polymorphic site existing at the 3'end is improved, in comparison with a primer having a nucleoside with a base complementary to a target gene at the second position from 3'end (Non-patent Document 1). However, even though this method is used, in some cases, such a primer extension product is obtained even when mismatches exist at the 3'end of the primer, and eventually, the method still had a problem in terms of detection sensitivity.

Further, a method using an oligonucleotide as a primer has been reported (Patent Document 1), in which the 3'end of the nucleotide sequence thereof is set in a polymorphic site, and a 2'-O, 4'-C-ethylene nucleotide unit is used as the third nucleotide from 3'end thereof.

In the above-described Patent Document, using a primer complementary to a wild type sequence in which the third nucleotide from 3'end thereof is a 2'-O,4'-C-ethylene nucleotide unit (Example 1 of Patent Document 1) and a primer complementary to a mutant type sequence in which the third nucleotide from 3' end thereof is a 2'-O,4'-C-ethylene nucleotide unit (Example 2 of Patent Document 1), PCR has been performed using a wild type sample as a template (Test Example 1 of Patent Document 1). In this case, amplification of gene was confirmed when the primer complementary to the wild type DNA sequence was used, and amplification of gene was not confirmed when the primer complementary to the mutant type DNA sequence was used. For this reason, in the above-described reference, it has been stated that the selective amplification of gene can be performed by this method.

However, it cannot be concluded only by the above-described results that the above-described primer, which is complementary to the wild type sequence, is specific for the detection of the wild type. That is, unless the result showing that when PCR with a wild type DNA sample as a template is performed by using a primer complementary to a wild type sequence, the primer extension products can be obtained, however, when PCR with a mutant type DNA sample as a template is performed by using the same primer, the primer extension products can not be obtained, there can not be a proof showing that the above-described primer is capable of detecting wild type specifically.

In fact, even when PCR is performed using "a primer which amplifies mutant type" and a sample from wild type gene according to this method, there is a problem that the primer extension products is obtained (emergence of false positive). Namely, there is a problem that even when the primer extension product could be obtained by performing PCR using this primer for a sample, which sample is unclear whether it is wild type or mutant type, still the sample cannot be determined whether it is wild type.

As to a possible cause of the above-described problem, the following reason can be considered. That is, the thermostable DNA polymerase used for PCR has a 5'→3' polymerase activity and concurrently has a 3'→5' exonuclease activity. Therefore, when a primer capable of amplifying the mutant type is bound to a sample comprising the wild type gene, the nucleotide base allocated at the 3'end of the primer, which base is the same or complementary to the mutant nucleotide gene, will be cleaved at the PCR step by the 3'→5' exonuclease activity of the thermostable DNA polymerase. Therefore, the 3' end of the above-described primer recognizes completely the gene sequence of the wild type sample, which normally should not be recognized, and the extension reaction according to the primer sequence is started by the action of the DNA polymerase. In consequence, it is considered that, even though a primer which should amplify the mutant type has been used, and PCR has been performed using a sample comprising wild type gene as a template, the primer extension product has been produced, and thus such a nonspecific amplification is occurred.

In addition, in general, the "specificity" is defined as the ability to give a decision for negative as negative. And so, as a method for improving the specificity in the analysis of mutation and polymorphism using a nucleic acid amplification reaction, a method for inhibiting nonspecific amplification (emergence of false positive amplification) can be considered. As a means for this purpose, optimization of amplification condition (increase of anneal temperature, decrease of cycle number, lowering of enzyme amount, change of enzyme species, decrease of dNTP concentration, decrease of Mg concentration, decrease of template DNA concentration, and the like), modification of primer design, utilization of hot start method using antibody or aptamer, utilization of modified oligonucleotide (PNA and LNA, and the like) which have been said to increase the specificity, and the like are considered. However, there are some cases where these methods are effective for the suppression of nonspecific amplification, but in many cases the effectiveness is insufficient and optionally the suppression is also occurred in the specific amplification, and these each has drawback.

From these circumstances, establishment of a method for detecting mutation(s) in nucleotide sequence with exclusion of false positive and with high specificity has been desired.

Patent Document 1: JP-A-2005-323583
Patent Document 2: JP-A-1993-271224
Non-patent Document 1: Bioorganic & Medical Chemistry, 2003, vol. 11, pp. 2211-2226
Non-patent Document 2: VIVEK KAPUR et al., J. Clin. Microbiol., vol. 32, No. 4, 1994, pp. 1095-1098
Non-patent Document3: Koji Morita et al., Bioorganic & Medical Chemistry Letters, vol. 12, 2002, pp. 73-76

DISCLOSURE OF THE INVENTION

Problem to be Solved by the Invention

It is an object of the present invention to provide a method for detecting mutation(s) in nucleotide sequence with improved specificity and a kit for detecting genetic polymorphism.

Means for Solving Problems

The present invention has been made for the purpose of solving the above-described problems, and comprises the following constituents (I) and (II).
(I) A method for detecting mutation(s) in nucleotide sequence comprising:
  performing a nucleic acid amplification reaction by using any one of the following oligonucleotides (a) to (d) or a salt thereof as a primer, and using a nucleic acid in a sample as a template, and
  detecting reaction product;
  (a) an oligonucleotide,
    i) wherein the oligonucleotide has the same nucleotide as a mutant nucleotide in a target gene at the 3'end position thereof,
    ii) wherein the oligonucleotide has the same nucleotide sequence as a nucleotide sequence of the target gene except for its 3'end position, and has the same nucleotide sequence as the nucleotide sequence of the target gene toward the 5'-side from the position where the mutant nucleotide may exist in the target gene, and
    iii) wherein the nucleotide at the second position from the 3'end thereof has a modification capable of inhibiting a reaction of nucleic acid synthesis,
  or a salt thereof;
  (b) an oligonucleotide,
    i) wherein the oligonucleotide has a nucleotide complementary to a mutant nucleotide in a target gene at the 3'end position thereof, ii) wherein the oligonucleotide has a nucleotide sequence complementary to a nucleotide sequence of the target gene except for its 3'end position, and has a nucleotide sequence complementary to the nucleotide sequence of the target gene toward the 3'-side from a position where the mutant nucleotide may exist in the target gene, and iii) wherein the nucleotide at the second position from the 3'end thereof has a modification capable of inhibiting a reaction of nucleic acid synthesis, or a salt thereof;

(c) an oligonucleotide, i) wherein the oligonucleotide has the same nucleotide as a reference nucleotide in a target gene at the 3'end position thereof, ii) wherein the oligonucleotide has the same sequence as a nucleotide sequence of the target gene except for its 3'end position, and has the same nucleotide sequence as the nucleotide sequence of the target gene toward the 5'-side from a position where the reference nucleotide exist in the target gene, and iii) wherein the nucleotide at the second position from the 3'end thereof has a modification capable of inhibiting a reaction of nucleic acid synthesis, or a salt thereof;

(d) an oligonucleotide, i) wherein the oligonucleotide has a nucleotide complementary to a reference nucleotide in a target gene at the 3'end position thereof, ii) wherein the oligonucleotide has a nucleotide sequence complementary to a nucleotide sequence of the target gene except for its 3'end position, and has a nucleotide sequence complementary to the nucleotide sequence of the target gene toward the 3'-side from a position where the reference nucleotide exist in the target gene, and iii) wherein the nucleotide at the second position from the 3'end thereof has a modification capable of inhibiting a reaction of nucleic acid synthesis, or a salt thereof.

(II) A kit for detecting mutation(s) in nucleotide sequence, comprising any one of the following oligonucleotides (a) to (d) or a salt thereof as a primer:

(a) an oligonucleotide, i) wherein the oligonucleotide has the same nucleotide as a mutant nucleotide in a target gene at the 3'end position thereof, ii) wherein the oligonucleotide has the same sequence as a nucleotide sequence of the target gene except for its 3'end position, and has the same nucleotide sequence as the nucleotide sequence of the target gene toward the 5'-side from the position where the mutant nucleotide may exist in the target gene, and iii) wherein the nucleotide at the second position from the 3'end thereof has a modification capable of inhibiting a reaction of nucleic acid synthesis, or a salt thereof;

(b) an oligonucleotide, i) wherein the oligonucleotide has a nucleotide complementary to a mutant nucleotide in a target gene at the 3'end position thereof, ii) wherein the oligonucleotide has a nucleotide sequence complementary to a nucleotide sequence of the target gene except for its 3'end position, and has a nucleotide sequence complementary to the nucleotide sequence of the target gene toward the 3'-side from a position where the mutant nucleotide may exist in the target gene, and iii) wherein the nucleotide at the second position from the 3'end thereof has a modification capable of inhibiting a reaction of nucleic acid synthesis, or a salt thereof;

(c) an oligonucleotide, i) wherein the oligonucleotide has the same nucleotide as a reference nucleotide in a target gene at the 3'end position thereof, ii) wherein the oligonucleotide has the same sequence as a nucleotide sequence of the target gene except for its 3'end position, and has the same nucleotide sequence as the nucleotide sequence of the target gene toward the 5'-side from a position where the reference nucleotide exist in the target gene, and iii) wherein the nucleotide at the second position from the 3'end thereof has a modification capable of inhibiting a reaction of nucleic acid synthesis, or a salt thereof;

(d) an oligonucleotide, i) wherein the oligonucleotide has a nucleotide complementary to a reference nucleotide in a target gene at the 3'end position thereof, ii) wherein the oligonucleotide has a nucleotide sequence complementary to a nucleotide sequence of the target gene except for its 3'end position, and has a nucleotide sequence complementary to the nucleotide sequence of the target gene toward the 3'-side from a position where the reference nucleotide exist in the target gene, and iii) wherein the nucleotide at the second position from the 3'end thereof has a modification capable of inhibiting a reaction of nucleic acid synthesis, or a salt thereof.

The present inventor has studied to solve the above-described problems with respect to the method for detecting a gene mutation. As a result, an oligonucleotide in which, once the position of gene mutation is designed to be at the 3'end thereof, and a nucleotide having a modification capable of inhibiting a reaction of nucleic acid synthesis (optionally described as "nucleotide analog") is disposed at the second position from 3'end thereof, was designed. And then the present inventor has found that when this oligonucleotide is used as a primer for PCR, all the problems as described above, for example, reading mistake of the template occurred when a single base deletion is caused by the 3'→5' exonuclease activity of the DNA polymerase utilized, can be solved, and as the result, the generation of false positive result in the primer extension product is suppressed, and the genetic mutation can be detected with high precision, and thus completed the present invention.

Effects of the Invention

The detection method of the present invention can be used, for example, for the microbial sensitivity test to check the resistance characteristics of bacteria which has been an essential test in the diagnosis (treatment) of tuberculosis. In particular, by using in-line (on chip PCR system) separation detection method, the gene diagnosis and determination of drug resistance of tubercle bacillus and nontuberculous acid-fast bacterium disease can be performed at the same time in a single tube (in a single line). This is a point of great advantage.

Particularly, in tubercle bacilli, 90 to 95% of rifampicin-resistant bacteria have a mutation in rpoB gene. And so, if the detection method of the present invention is performed, a mutation of the tubercle bacillus isolated from patient can be detected in a short time. By doing this, it will be possible to determine whether the patient is infected with rifampicin-resistant bacteria in short order, and to treat promptly. In addition, according to the present invention, the possibility of plural number of mutations in rpoB gene of the rifampicin-resistant bacteria can be detected and determined at once.

BEST MODE FOR CARRYING OUT THE INVENTION

Figure 1:
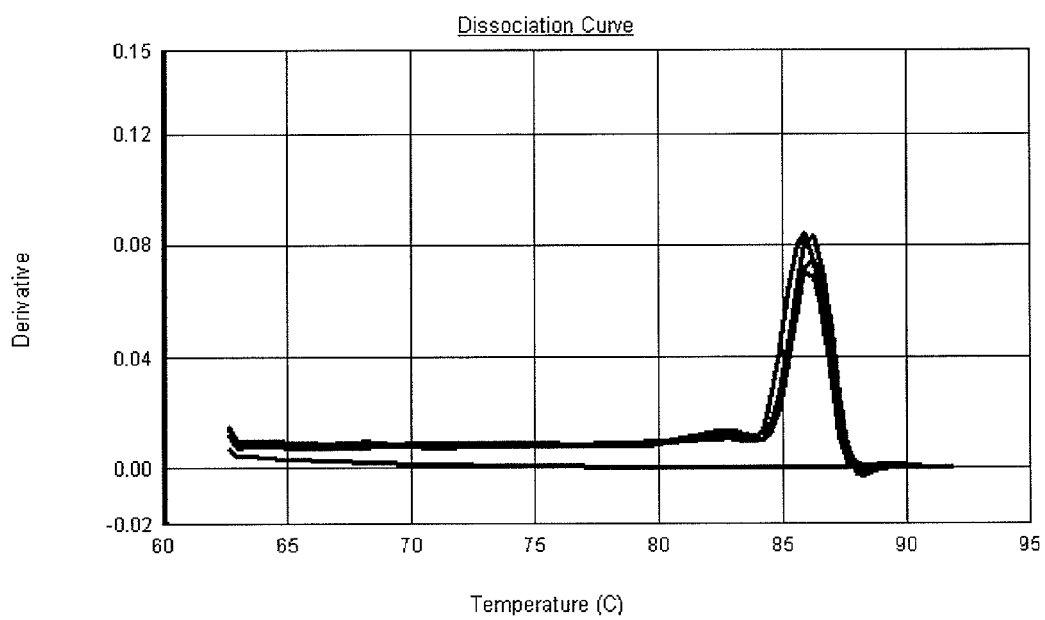
FIG. 1 shows a result of analysis of melting curve obtained based on the results of the real-time PCR by the intercalator method using the Primer rpoB_2 and using plasmid DNA comprising mutant type rpoB gene sequence_2 as a template obtained in Example 1.

The method for detecting mutation(s) in nucleotide sequence according to the present invention is "A method for detecting mutation(s) in nucleotide sequence comprising:

performing a nucleic acid amplification reaction by using any one of the following oligonucleotides (a) to (d) or a salt thereof as a primer, and using a nucleic acid in a sample as a template, and detecting reaction product;

(a) an oligonucleotide,
i) wherein the oligonucleotide has the same nucleotide as a mutant nucleotide in a target gene at the 3'end position thereof,
ii) wherein the oligonucleotide has the same nucleotide sequence as a nucleotide sequence of the target gene except for its 3'end position, and has the same nucleotide sequence as the nucleotide sequence of the target gene toward the 5'-side from the position where the mutant nucleotide may exist in the target gene, and
iii) wherein the nucleotide at the second position from the 3'end thereof has a modification capable of inhibiting a reaction of nucleic acid synthesis, or a salt thereof;

(b) an oligonucleotide,
i) wherein the oligonucleotide has a nucleotide complementary to a mutant nucleotide in a target gene at the 3'end position thereof,
ii) wherein the oligonucleotide has a nucleotide sequence complementary to a nucleotide sequence of the target gene except for its 3'end position, and has a nucleotide sequence complementary to the nucleotide sequence of the target gene toward the 3'-side from a position where the mutant nucleotide may exist in the target gene, and
iii) wherein the nucleotide at the second position from the 3'end thereof has a modification capable of inhibiting a reaction of nucleic acid synthesis, or a salt thereof;

(c) an oligonucleotide,
i) wherein the oligonucleotide has the same nucleotide as a reference nucleotide in a target gene at the 3'end position thereof,
ii) wherein the oligonucleotide has the same sequence as a nucleotide sequence of the target gene except for its 3'end position, and has the same nucleotide sequence as the nucleotide sequence of the target gene toward the 5'-side from a position where the reference nucleotide exist in the target gene, and
iii) wherein the nucleotide at the second position from the 3'end thereof has a modification capable of inhibiting a reaction of nucleic acid synthesis, or a salt thereof;

(d) an oligonucleotide,
i) wherein the oligonucleotide has a nucleotide complementary to a reference nucleotide in a target gene at the 3'end position thereof,
ii) wherein the oligonucleotide has a nucleotide sequence complementary to a nucleotide sequence of the target gene except for its 3'end position, and has a nucleotide sequence complementary to the nucleotide sequence of the target gene toward the 3'-side from a position where the reference nucleotide exist in the target gene, and
iii) wherein the nucleotide at the second position from the 3'end thereof has a modification capable of inhibiting a reaction of nucleic acid synthesis, or a salt thereof."

In the present invention, the term "mutation(s) in nucleotide sequence" includes, for example, "genetic polymorphism". The term "genetic polymorphism" is, as used in this field in the customary sense, and also referred to as SNP (single nucleotide polymorphism).

Specifically, for example, in a certain gene locus, a single base substitution that means substitution of a single base with another base, a single base deletion that means a single base is deleted, and a single base insertion that means a single base is inserted, are included.

In the present invention, it should be noted that, "mutation" and "base polymorphism" are referred to having a different nucleotide sequence from the wild type sequence. Generally, the mutation frequency of less than 1% is referred to as "mutation", and that of 1% or more is referred to as polymorphism. However, rigid distinction in wording should not be intended in the present specification.

The term "target gene" in the present invention includes a gene to be targeted in the detection of mutation(s) in nucleotide sequence, at least a region of the nucleotide sequence is known, and a has a possibility of mutation(s) in nucleotide sequence. Specifically, for example, genes such as rpoB gene of human tubercle bacillus (Non-patent Document 2), cytochrome P4501A2, cytochrome P4502A6, cytochrome P4502C9, cytochrome P4502C19, cytochrome P4502D6, cytochrome P4502E1, thiopurine methyltransferase, N-acetyltransferase, UDP-glucuronosyltransferase, glutathione S-transferase, HLA, TCRα, APOE4, dopamine D3 receptor, tryptophan hydroxylase, angiotensin precursor, blood coagulation factor VII, leptin and the like are included.

It should be noted that the number of mutation(s) in a gene is not specifically limited.

In the present invention, a nucleotide sequence which has not caused the "mutation(s) in nucleotide sequence" such as mutation (substitution), deletion and insertion as stated in the present invention (for example, nucleotide sequence of gene of wild type bacteria) is referred to as a "reference sequence". In addition, in the reference sequence, a nucleotide at the position where the mutation may be caused is referred to as a "reference nucleotide". Also, "mutant nucleotide" is referred to as a nucleotide at the mutation position where the mutation has been caused for the reference sequence.

In the present invention, the term "complementary nucleotide" is used for meaning in the customary sense in this field. That is, it refers to a nucleotide composed of a nucleic acid base which is complementary to the base of the target nucleotide.

In the present invention, the nucleic acid base composing a nucleotide may be represented by the abbreviations (adenine as "A", guanine as "G", cytosine as "C", and thymine as "T") as used customarily in the field of the present invention.

The term "salt" used in the "oligonucleotide or the salt thereof" of the present invention includes, for example, salts of alkaline metal such as sodium, potassium, or lithium; salts of alkaline earth metal such as calcium or magnesium; salts of metal such as aluminum, iron, zinc, copper, nickel, or cobalt; inorganic salts such as ammonium salt; organic acid salts such as salts of amine such as t-octylamine, dibenzylamine, morpholine, ethylenediamine, N-methylglucamine, guanidine, diethylamine, triethylamine, dicyclohexylamine, N,N'-dibenzylethylenediamine, chloroprocaine, procaine, diethanolamine, N-benzyl-phenethylamine, piperazine, tetramethylammonium, or tris(hydroxymethylaminomethane); salts of amino acid such as glycine, lysine, arginine, ornithine, glutamic acid, or aspartic acid.

In the term "nucleotide having a modification capable of inhibiting a reaction of nucleic acid synthesis" in the present invention, the term "having a modification capable of inhibiting a reaction of nucleic acid synthesis" means the use of, for example, a ribose derivative or an oxetane derivative having a structure "capable of inhibiting a reaction of nucleic acid synthesis" in place of, for example, normal 2-deoxy-D-ribose composing a nucleotide. And the nucleotide or the salt thereof having such modification is the one which inhibits the reaction of nucleic acid synthesis and does not provide any replication products (amplification products), when the nucleic acid amplification reaction described hereinafter is performed using an oligonucleotide wherein this nucleotide is set at the 3' end thereof as a primer.

A specific example of the "nucleotide having a modification capable of inhibiting a reaction of nucleic acid synthesis" in the present invention includes, for example, a nucleotide derivative represented by the following formula [I] or [II],

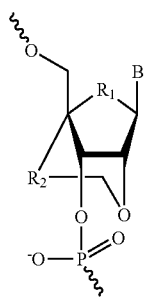

[I]

wherein B represents a nucleic acid base; $R_1$ represents an oxygen atom, a —NH-group or a lower alkylene group; $R_2$ represents a lower alkylene group;

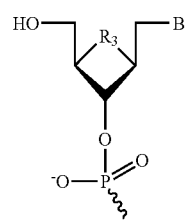

[II]

wherein B represents a nucleic acid base; $R_3$ represents an oxygen atom, a nitrogen atom, a —NH-group or a lower alkylene group.

In the above-described formula [I] and formula [II], the lower alkylene group shown as $R_1$, $R_2$ and $R_3$ include methylene group, ethylene group, propylene group, butylene group, pentylene group, and hexylene group (these may be either straight chain, branched chain or cyclic.).

The specific examples of the nucleotide having a modification capable of inhibiting a reaction of nucleic acid synthesis represented by the formula [I] of the present invention are shown in Table 1 below.

TABLE 1

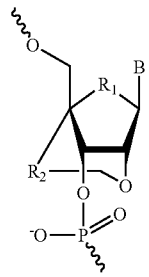

[I]

| No. | R1 | R2 | Name |
|---|---|---|---|
| 1 | O | CH$_2$ | 2'-O,4'-C-Ethylene-bridged Nucleic Acids (ENA) |
| 2 | O | (CH$_2$)$_2$ | 2'-O,4'-C-Propylene-bridged Nucleic Acids |
| 3 | O | (CH$_2$)$_3$ | 2'-O,4'-C-Buthylene-bridged Nucleic Acids |
| 4 | O | (CH$_2$)$_4$ | 2'-O,4'-C-Pentylene-bridged Nucleic Acids |
| 5 | CH$_2$ | CH$_2$ | 2'-O,4'-C-Ethylene-bridged C-Analogue Nucleic Acids |
| 6 | CH$_2$ | (CH$_2$)$_2$ | 2'-O,4'-C-Propylene-bridged C-Analogue Nucleic Acids |
| 7 | CH$_2$ | (CH$_2$)$_3$ | 2'-O,4'-C-Buthylene-bridged C-Analogue Nucleic Acids |
| 8 | CH$_2$ | (CH$_2$)$_4$ | 2'-O,4'-C-Pentylene-bridged C-Analogue Nucleic Acids |
| 9 | S | CH$_2$ | 2'-O,4'-C-Ethylene-bridged S-Analogue Nucleic Acids |
| 10 | S | (CH$_2$)$_2$ | 2'-O,4'-C-Propylene-bridged S-Analogue Nucleic Acids |
| 11 | S | (CH$_2$)$_3$ | 2'-O,4'-C-Buthylene-bridged S-Analogue Nucleic Acids |
| 12 | S | (CH$_2$)$_4$ | 2'-O,4'-C-Pentylene-bridged S-Analogue Nucleic Acids |
| 13 | NH | CH$_2$ | 2'-O,4'-C-Ethylene-bridged N-Analogue Nucleic Acids |
| 14 | NH | (CH$_2$)$_2$ | 2'-O,4'-C-Propylene-bridged N-Analogue Nucleic Acids |
| 15 | NH | (CH$_2$)$_3$ | 2'-O,4'-C-Buthylene-bridged N-Analogue Nucleic Acids |
| 16 | NH | (CH$_2$)$_4$ | 2'-O,4'-C-Pentylene-bridged N-Analogue Nucleic Acids |

The specific examples of the nucleotide having a modification capable of inhibiting a reaction of nucleic acid synthesis represented by the formula [II] of the present invention are shown in Table 2 below.

TABLE 2

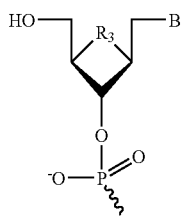

[II]

| No. | R$_3$ | Name |
|---|---|---|
| 17 | O | Nucleotide Derivative Containing Oxetane Ring |
| 18 | CH$_2$ | Nucleotide Derivative Containing Cyclobutane Ring |
| 19 | S | Nucleotide Derivative Containing Thiethane Ring |
| 20 | NH | Nucleotide Derivative Containing Azetidine Ring |
| 21 | CH$_2$ | Nucleotide Derivative Containing Cyclobutane Ring |

The "nucleotide having a modification capable of inhibiting a reaction of nucleic acid synthesis" represented by the formula [I] of the present invention can be synthesized using appropriate materials according to a synthetic method described, for example, in Koji Morita et al., Bioorganic & Medicinal Chemistry Letters, vol. 12, 2002, p. 73-76 (Non-patent Document 3). In this regard, 2'-O,4'-C-Ethylene-bridged Nucleic Acids (ENA) is commercially available and can the commercially available products may be employed in the present invention.

The "nucleotide having a modification capable of inhibiting a reaction of nucleic acid synthesis" represented by the formula [II] of the present invention can be synthesized using appropriate materials according to a synthetic method described, for example, in JP-A-1993-271224 (Patent Document 2).

It should be noted that, as to the "nucleotide having a modification capable of inhibiting a reaction of nucleic acid synthesis" of the present invention, any kind of nucleotide which has the same property as described above can be used, and the nucleotides are not limited to the nucleotides shown in Table 1 and Table 2.

The primer of the present invention includes, (a) an oligonucleotide, i) wherein the oligonucleotide has the same nucleotide as a mutant nucleotide in a target gene at the 3'end position thereof, ii) wherein the oligonucleotide has the same nucleotide sequence as a nucleotide sequence of the target gene except for its 3'end position, and has the same nucleotide sequence as the nucleotide sequence of the target gene toward the 5'-side from the position where the mutant nucleotide may exist in the target gene, and iii) wherein the nucleotide at the second position from the 3'end thereof has a modification capable of inhibiting a reaction of nucleic acid synthesis, or a salt thereof (hereinafter, optionally referred to as "Primer a");

(b) an oligonucleotide, i) wherein the oligonucleotide has a nucleotide complementary to a mutant nucleotide in a target gene at the 3'end position thereof, ii) wherein the oligonucleotide has a nucleotide sequence complementary to a nucleotide sequence of the target gene except for its 3'end position, and has a nucleotide sequence complementary to the nucleotide sequence of the target gene toward the 3'-side from a position where the mutant nucleotide may exist in the target gene, and iii) wherein the nucleotide at the second position from the 3'end thereof has a modification capable of inhibiting a reaction of nucleic acid synthesis,
c) an oligonucleotide,
  i) wherein the oligonucleotide has the same nucleotide as a reference nucleotide in a target gene at the 3'end position thereof,
  ii) wherein the oligonucleotide has the same sequence as a nucleotide sequence of the target gene except for its 3'end position, and has the same nucleotide sequence as the nucleotide sequence of the target gene toward the 5'-side from a position where the reference nucleotide exist in the target gene, and
  iii) wherein the nucleotide at the second position from the 3'end thereof has a modification capable of inhibiting a reaction of nucleic acid synthesis,
or a salt thereof (hereinafter, optionally referred to as "Primer c");
(d) an oligonucleotide,
  i) wherein the oligonucleotide has a nucleotide complementary to a reference nucleotide in a target gene at the 3'end position thereof,
  ii) wherein the oligonucleotide has a nucleotide sequence complementary to a nucleotide sequence of the target gene except for its 3'end position, and has a nucleotide sequence complementary to the nucleotide sequence of the target gene toward the 3'-side from a position where the reference nucleotide exist in the target gene, and
  iii) wherein the nucleotide at the second position from the 3'end thereof has a modification capable of inhibiting a reaction of nucleic acid synthesis,
or a salt thereof (hereinafter, optionally referred to as "Primer d").

For example, when the Primer a of the present invention is designed, an oligonucleotide comprising a part or entire of the same nucleotide sequence as the nucleotide sequence of the target gene toward the 5'-side from the position in the above-described target gene where the mutant nucleotide of the detection target may exist, except that the mutant nucleotide in the genetic mutation (for example, genetic polymorphism) of detection target is set at the 3'end thereof, and a nucleotide having a modification capable of inhibiting a reaction of nucleic acid synthesis is set at the nucleotide at the second position from 3'end" is designed; and then in consideration of the melting temperature (Tm value) and the like, the primer with an appropriate length of appropriate region may be designed from the above-described oligonucleotide.

When the Primer b is designed, an oligonucleotide in which a nucleotide complementary to a mutant nucleotide (for example, genetic polymorphism) in a target gene is set at the 3'end thereof, and the other region of the oligonucleotide is an oligonucleotide comprising a part or entire of the nucleotide sequence complementary to the nucleotide sequence of the above-described target gene toward the 3'-side from the position where the mutant nucleotide may exist in the above-described target gene, and the nucleotide at the second position from the 3'end thereof has a modification capable of inhibiting a reaction of nucleic acid synthesis as described above, may be designed; and then in consideration of the melting temperature (Tm value) and the like, the primer with an appropriate length of appropriate region may be designed from the above-described oligonucleotides.

When the Primer c is designed, a oligonucleotide in which the same nucleotide as a "reference nucleotide at the position in the target gene where the mutation may be caused" is set at the 3'end thereof, and the region except for its 3'end position is the same sequence as a nucleotide sequence (reference sequence) of the target gene, and has the same sequence as the nucleotide sequence of the target gene toward the 5'-side from a position where the reference nucleotide exist in the above-described target gene, and the nucleotide at the second position from the 3'end thereof has the modification capable of inhibiting a reaction of nucleic acid synthesis is designed; and then in consideration of the melting temperature (Tm value) and the like, the primer with an appropriate length of appropriate region may be designed from the above-described oligonucleotide.

When the Primer d is designed, an oligonucleotide in which a nucleotide complementary to the "reference nucleotide at the position in the target gene where a mutation may be caused" is set at the 3'end thereof, and the region except for its 3'end is complementary to the nucleotide sequence (reference sequence) of the target gene, and has the sequence complementary to the nucleotide sequence of the target gene toward the 3'-side from the position in the above-described target gene where the above-described reference nucleotide exist; and the nucleotide at the second position from the 3'end thereof has the modification capable of inhibiting a reaction of nucleic acid synthesis is designed; and ten in consideration of the melting temperature (Tm value) and the like, the primer with an appropriate length of appropriate region may be designed from the above-described oligonucleotide.

The length of the primer of the present invention includes, preferably 10 bases or more, which has been considered for the base number necessary to maintain the specificity as primer sequence, and a primer having the length with 20 or more of bases is more preferable. For example, the ones comprised of 15 to 30 bases are included.

In order to obtain the primer of the present invention, it is preferable to prepare by the method of chemical synthesis well known per se, using a nucleotide which has a modification capable of inhibiting a reaction of nucleic acid synthesis of the present invention obtained by the above-described method and a normal nucleotide. By this method, an oligonucleotide with constant quality can be obtained, easily, in large amount at low cost.

For example, an oligonucleotide is synthesized using a DNA synthesizer usually used for the DNA synthesis by the commonly used phosphoramidite method, then purified by the conventional method using an anion-exchange column chromatography, and thus the objective oligonucleotide of the present invention can be obtained.

It should be noted that the oligonucleotides having a "nucleotide which has a modification capable of inhibiting a reaction of nucleic acid synthesis" of the present invention is available through the use of vendor's custom service of nucleic acid synthesis.

The principle of the method for detecting mutation(s) in nucleotide sequence according to the present invention is described as follows:
<Principle 1> the Primer a or the Primer b of the Present Invention is Used:

For example, when mutation in nucleotide sequence of a single-base mutation is intended to be detected, above-described Primer a or Primer b, an oligonucleotide primer capable of amplifying a sequence of interest by the nucleic acid amplification reaction in pairs with the above described primer, and a sample (nucleic acid comprising a nucleotide sequence to be detected for mutation in nucleotide sequence) are subjected to the nucleic acid amplification reaction in a reaction solution. And, if the nucleotide of 3'end of the Primer a or the nucleotide of 3'end of the Primer b matches (or the base is complementary), namely if there exist a single-base mutation, the nucleic acid amplification reaction takes place.

In contrast, if the nucleotide of the 3'end does not match (or the base is not complementary), namely if there exist no single-base mutation, the nucleic acid amplification reaction does not take place.

<Principle 2> the Primer c or the Primer d of the Present Invention is Used:

For example, when mutation(s) in nucleotide sequence of a single-base mutation is intended to be detected, above-described Primer c or Primer d, an oligonucleotide primer capable of amplifying a sequence of interest by the nucleic acid amplification reaction in pairs with the above-described primer, and a sample (nucleic acid comprising a nucleotide sequence to be detected for mutation(s) in nucleotide sequence) are subjected to the nucleic acid amplification reaction in a reaction solution. And, if the nucleotide of 3'end of the Primer c or the nucleotide of 3'end of the Primer d matches (or the base is complementary), namely if there exist the same nucleotide as the reference nucleotide of detection target, the nucleic acid amplification reaction takes place. In contrast, if the nucleotide of 3'end does not match (or the base is not complementary), namely if there exist a single-base mutation, the nucleic acid amplification reaction does not take place.

For example, focusing on the mutation of rpoB gene of human tubercle bacillus as a genetic polymorphism to be detected, the Primer a to be used when the detection is performed according to the above-described <Principle 1> may be designed as follows.

Namely, for the detection of a mutation in rpoB gene, an oligonucleotide or the salt thereof in a target gene, (i) wherein the oligonucleotide has the same nucleotide as a mutant nucleotide having a mutant base at the 3'end position thereof, and (ii) wherein the oligonucleotide has the same nucleotide sequence except for its 3'end position, as the nucleotide sequence of rpoB gene toward the 5'-side from the position in rpoB gene where the above-described mutant nucleotide may exist, and (iii) wherein the nucleotide at the second position from the 3'end thereof has a modification capable of inhibiting a reaction of nucleic acid synthesis, may be designed.

Focusing on the mutation of rpoB gene of human tubercle bacillus as a genetic polymorphism to be detected, the Primer c to be used when the detection is performed according to the above-described <Principle 2> may be designed as follows.

Namely, for the detection of a mutation in rpoB gene, an oligonucleotide or the salt thereof, (i) wherein the oligonucleotide has the same nucleotide as the reference nucleotide in rpoB gene at the 3'end position thereof; and, (ii) wherein the oligonucleotide has the same nucleotide sequence as the nucleotide sequence of rpoB gene at the position except for its 3'end position, and has the same nucleotide sequence as the nucleotide sequence of the rpoB gene toward the 5'-side from a position where the above-described reference nucleotide exist in rpoB gene, and (iii) wherein the nucleotide at the second position from the 3'end thereof has a modification capable of inhibiting a reaction of nucleic acid synthesis; may be designed.

As to the method for designing a primer of the present invention, for example, a specific example of designing the Primer a for detecting mutation of rpoB gene by the method based on the <Principle 1> is described below.

The rpoB gene of human tubercle bacillus and the type of mutation for rifampcin resistance (RFP resistance) and its position in the gene have been described in FIG. 1 of VIVEK KAPUR et al., J. Clin. Microbiol., vol. 32, No. 4, 1994. p 1095-1098 (Non-patent Document 2). Therefore, referring the description in this FIG. 1, at first, a sequence comprising a single-base mutation is designed.

For example, in rpoB gene of the wild type human tubercle bacillus, the mutation exists in some cases at the oligonucleotide region of 69 base pairs coding for the $511^{th}$ to $533^{rd}$ amino acids.

The oligonucleotide sequence of these 69 base pairs of the wild type human tubercle bacillus (hereinafter, referred to as "the sequence of a hot spot mutation region in the wild type rpoB gene") is as follows.

(SEQ ID NO:1)
5'-CTGAGCCAATTCATGGACCAGAACAACCCGCTGTCGGGGTTGACCCA

CAAGCGCCGACTGTCGGCGCTGGGG-3'

And, as one of the mutations of this region, in the sequence of a hot spot mutation region in the wild type rpoB gene, the $46^{th}$ base "C" (cytosine) from the 5' end in the sequence of the above-described SEQ ID NO:1 is possible to be changed to "T" (thymine). Consequently, an oligonucleotide with the following sequence and yet with a functional length as a primer can be designed so that this mutation would be exist at 3'end (namely, its 3'end would be "T"), and also the other region of it would be the same sequence as the nucleotide sequence of wild type rpoB gene toward the 5'-side from the above-described $46^{th}$ base in the sequence of a hot spot mutation region in the wild type rpoB gene. The underlined base corresponds to the mutant base.

5'-GCTGTCGGGGTTGACC<u>T</u>-3'     (SEQ ID NO:7)

In the next place, the second base "C" from the 3'end in the above-described sequence is designed to be the "C" having "a modification capable of inhibiting a reaction of nucleic acid synthesis of the present invention". This is hereinafter referred to as "Primer rpoB_2".

When the nucleic acid amplification reaction (PCR) is performed by using this primer, existence or nonexistence of the mutation at the $46^{th}$ base "C" to "T" in the sequence of a hot spot mutation region in the wild type rpoB gene can be detected.

In addition, in an example of another mutation, as to the oligonucleotide of SEQ ID NO:1, in the sequence of the hot spot mutation region in the wild type rpoB gene, the $68^{th}$ base "T" from the 5' end in the sequence is possible to be changed to "C". Consequently, an oligonucleotide with the following sequence and yet with a functional length as a primer can be designed so that this mutation would exist at 3'end (namely, 3'end would be "C"), and also the other region of it would be the same sequence as the nucleotide sequence of wild type rpoB gene toward the 5'-side from the above-described $68^{th}$ base in the sequence of a hot spot mutation region in the wild type rpoB gene. The underlined base corresponds to the mutant base.

5'-CCGACTGTCGGCGC<u>C</u>-3'     (SEQ ID NO:8)

In the next place, the second base "C" from the 3'end in the above-described sequence is designed to be the "C" having "a modification capable of inhibiting a reaction of nucleic acid synthesis of the present invention". This is hereinafter referred to as "Primer rpoB_6".

If the nucleic acid amplification reaction (PCR) is performed using this primer, existence or nonexistence of the mutation at the $68^{th}$ base "T" to "C" in the sequence of a hot spot mutation region in the wild type rpoB gene can be detected.

Further, in an example of another mutation, as to an oligonucleotide of SEQ ID NO:1, in the sequence of the hot spot mutation region in the wild type rpoB gene, the 46$^{th}$ base "C" from the 5' end in the sequence is possible to be changed to "G" (guanine). Consequently, an oligonucleotide with the following sequence and yet with a functional length as a primer can be designed so that this mutation would exist at 3'end (namely, its 3'end would be "G"), and also the other region of it would be the same sequence as the nucleotide sequence of wild type rpoB gene toward the 5'-side from the above-described 46$^{th}$ base in the sequence of a hot spot mutation region in the wild type rpoB gene. The underlined base corresponds to the mutant base.

```
5'-GCTGTCGGGGTTGACCG-3'         (SEQ ID NO:9)
```

In the next place, the second base "C" from the 3'end in the above-described sequence is designed to be "C" having "a modification capable of inhibiting a reaction of nucleic acid synthesis of the present invention". This is hereinafter referred to as "Primer rpoB_3".

When the nucleic acid amplification reaction (PCR) is performed using this primer, existence or nonexistence of the mutation at the 46$^{th}$ base "C" to "G" in the sequence of a hot spot mutation region in the wild type rpoB gene can be detected.

And further, in an example of another mutation, as to an oligonucleotide of SEQ ID NO:1, in the sequence of the hot spot mutation region in the wild type rpoB gene, the 47$^{th}$ base "A" (adenine) from the 5'end in the sequence is possible to be changed to "T". Consequently, an oligonucleotide with the following sequence and yet with a functional length as a primer can be designed so that this mutation would exist at 3'end (namely, its 3'end would be "T"), and also the other region of it would be the same sequence as the nucleotide sequence of wild type rpoB gene toward the 5'-side from the above-described 47$^{th}$ base in the sequence of a hot spot mutation region in the wild type rpoB gene. The underlined base corresponds to the mutant base.

```
5'-CTGTCGGGGTTGACCCT-3'         (SEQ ID NO:10)
```

In the next place, the second base "C" from the 3'end of the above-described sequence is designed to be "C" having "a modification capable of inhibiting a reaction of nucleic acid synthesis of the present invention". This is hereinafter referred to as "Primer rpoB_4".

When the nucleic acid amplification reaction (PCR) is performed by using this primer, existence or nonexistence of the mutation at the 47$^{th}$ base "A" to "T" in the sequence of a hot spot mutation region in the wild type rpoB gene can be detected.

The above-described examples are only the explanations of method of designing a primer of the present invention, and thus, when the other mutation would be detected, the oligonucleotides of the present invention of (a)-(d) or salt thereof having the structure as described above may be designed.

It should be noted that the primer of the present invention may be labeled with a labeling substance.

As to the labeling substance to be used for labeling the primer of the present invention with a labeling substance, any of the known labeling substances such as radioisotope, enzyme, fluorescent substance, luminescent substance and biotin may be used.

For example, radioisotope such as $^{32}$P, $^{33}$P and $^{35}$S, enzymes such as alkaline phosphatase and horseradish peroxidase, fluorescent substance such as Cyanine Dye series of Cy3, Cy5 (Amersham Biosciences K.K.), and fluorescein, luminescent substance such as chemoluminescent reagent comprising acridinium ester, are included.

When the primer of the present invention is labeled with radioisotope, a method of labeling by incorporation of a radioisotope-labeled nucleotide into the primer at the time when the primer is synthesized, or a method of labeling with radioisotope after the primer is synthesized or the like are included. Specifically, a frequently-used random primer method, nick-translation method, 5'-terminal labeling method using T4 polynucleotide kinase, 3'-terminal labeling method using terminal deoxynucleotidyl transferase and RNA labeling method are included. included.

When the primer of the present invention is labeled with an enzyme, the conventional technique in this field of direct labeling method by which the primer to be labeled is directly linked covalently with an enzyme molecule such as alkaline phosphatase, horseradish peroxidase or the like can be employed.

When the primer of the present invention is labeled with fluorescent substance, for example, the fluorescently labeled nucleotide can be incorporated into the primer by conventional labeling technique in this field. In addition, by a method of replacing a sequence with a nucleotide having a linker arm as a member of a oligonucleotide (See, for example, Nucleic Acids Res., 1986, vol. 14, p. 6115), the nucleotide can also be labeled with the fluorescent substance. In that case, there can also be a method that a uridine having a linker arm on 5-position is synthesized chemically from a deoxyuridine by a synthetic method disclosed in JP-A-1985-500717 and then a fluorescent substance is introduced into the above-described oligonucleotide.

In the methods of labeling with a luminescent substance and with biotin, the labeling can be carried out according to the conventional technique of luminescent-labeling or biotin-labeling of nucleotide usually conducted in this field.

An oligonucleotide primer capable of amplifying a sequence of interest by nucleic acid amplification reaction in pairs with the above-described primer of the present invention is an appropriate oligonucleotide capable of amplifying a sequence possible to contain the target mutant sequence (a sequence of interest) in the known sequence of detection target.

The method for designing "an oligonucleotide primer capable of amplifying a sequence of interest in pairs with the primer of the present invention by nucleic acid amplification reaction when the nucleic acid amplification reaction is performed by using an oligonucleotide of the present invention as a primer", and the method for obtaining thereof include, for example, a method which is designed so as to prevent interference reaction with the primer of the present invention through the use of a primer prediction software such as Primer 3 (Whitehead Institute for Biomedical Research).

In addition, if available, an oligonucleotide primer which has a characteristics of "an oligonucleotide primer capable of amplifying a sequence of interest in pairs with the primer of the present invention by the nucleic acid amplification reaction when the nucleic acid amplification reaction is performed by using an oligonucleotide of the present invention as the primer" as described above, and the one usually used in this field can be used. The various types of primers are commercialized (for example, M13 Forward Primer, TAKARA BIO INC.), and are also available.

The "nucleic acid amplification reaction" involved in the "method for detecting mutation(s) in nucleotide sequence of the present invention comprising: performing a nucleic acid amplification reaction by using the primer of the present invention" include, a conventional method usually conducted in this field in which, primer extension is performed using, for example, a primer of the present invention, by hybridizing this with a nucleic acid in a sample, and by conducting nucleic acid amplification with DNA polymerase and the like [for example, PCR (JP-A-1985-281), LAMP (Loop-mediated Isothermal Amplification) method (Tsugunori Notomi et al., Nucleic Acid Res., 28, e63, 2000), ICAN (Isothermal and Chimeric primer-initiated Amplification of Nucleic acids) method (Rinsho Byori (Jpn. J. Clin. Pathol.) 51(11), 1061-1067, 2003, Nov.), LCR (ligase chain reaction) method (JP-A-1992-211399), SDA (strand displacement amplification) method (JP-A-1996-19394)]. The reaction condition of the nucleic acid amplification reaction including PCR, the operation procedure and the like may be according to the conventional method usually used in this field.

The "method for detecting reaction product obtained by the nucleic acid amplification reaction" of the present invention includes various detection methods such as, for example, an intercalator method, a TaqMan™ real-time PCR method (see, for example, the specification of U.S. Pat. No. 5,538,848), MGB Eclipse Probe System method (see, for example, the specification of U.S. Pat. No. 5,801,155), Molecular Beacons Probe Technology method (see, for example, the specification of U.S. Pat. No. 5,925,517), LUX Fluorogenic Primer method (Invitrogen Corporation), Quenching probe-PCR (QP) method (see, for example, the specification of U.S. Pat. No. 6,492,121), a method in which, after the nucleic acid amplification reaction is performed, the primer extension products obtained are subjected to the electrophoresis, and the detection is performed based on the results of the electrophoresis, a method in which the determination is performed by measuring the signal derived from the primer extension product obtained by the nucleic acid amplification reaction using the labeled primer.

As to a method for determining amplification products (primer extension products) obtained by the nucleic acid amplification reaction, taking the following 4 methods for instance, an explanation will be given for each method; however, as a matter of course, it should not be limited thereto.

(1) Intercalator method.
(2) TaqMan™ real-time PCR method.
(3) a method in which, after the nucleic acid amplification reaction is performed, the primer extension products obtained are subjected to the electrophoresis, and the detection is performed based on the results of the electrophoresis,
(4) a method in which the determination is performed by measuring the signal derived from the primer extension product obtained by the nucleic acid amplification reaction using the labeled primer.

(1) Intercalator Method

The conventional intercalator method in which the real-time PCR is performed using known intercalator can be utilized.

For example, a method of performing the real-time PCR utilizing conventional intercalator method using a primer of the present invention and an oligonucleotide primer capable of amplifying a sequence of interest by nucleic acid amplification reaction in pairs with the above-described primer, is included.

The intercalator is a reagent capable of generating fluorescence by binding specifically with a double-stranded DNA, and generates fluorescence when exposed to excitation light. When the DNA is increased by repeated amplification of PCR, the intercalator is incorporated into the DNA accordingly. That is, as the amount of intercalator incorporated into DNA is proportional to the amount of the amplification product, the amount of the primer extension product can be determined by detecting the fluorescence intensity derived from the intercalator.

In this regard, however, as the intercalator binds to the entire double-stranded DNA, the melting curve analysis is performed based on the results of measurement of the fluorescent intensity. That is, after PCR, fluorescence intensity from the intercalator is measured in parallel with increasing the temperature of the reaction solution of PCR comprising the obtained amplification products. In the beginning, fluorescence is generated because the amplification product forms double strand. However, when the temperature of the reaction solution of PCR reaches to a certain temperature, the amplification products will dissociate to single strand, and the fluorescence intensity from the intercalator decreases immediately. The temperature at the time is the melting temperature (Tm value), and is an intrinsic value of the sequence of a primer extension product. A specific product (an objective product) and a non-specific product may be identified from this Tm value.

This intercalator method does not require electrophoresis after the real-time PCR, and therefore, is an effective method when the rapid determination of mutation(s) is required in such a case of clinical testing (diagnosis).

The intercalator to be used for the present invention includes, while any type of the intercalator usually used in this field, for example, SYBR™ Green I (Molecular Probes Inc.), ethidium bromide, fluorine and the like can be utilized.

The example of "the method for detecting mutation in nucleotide sequence by performing intercalator method" of the present invention would be explained as follows:

<Method (1)-1>

Using a Primer a or a Primer b of the present invention, an oligonucleotide primer capable of amplifying a sequence of interest by the nucleic acid amplification reaction in pairs with the above-described primer, and SYBR™ Green I as the intercallator, and using a purified DNA sample purified from a sample to be detected for mutation as a template, real-time PCR is performed using Taq DNA polymerase. And the fluorescent intensity emitted from SYBR™ Green I intercalated into the amplification products is measured.

In order to detect mutation, for example, analysis on the melting curve of amplification products may be performed. That is, the melting curve is made by plotting the melting temperature of amplification product (double-stranded DNA) as horizontal axis and the first derivation (variation) of fluorescent intensity as vertical axis, and detection of peak is examined. When the Tm value of the detected peak of each primer extension product is identical with that of the primer extension product predicted to be amplified by the real-time PCR using the same combination of primers, it can be determined that there is a objective, that is, mutation of detection target(s) in nucleotide sequence in the purified DNA sample.

In addition, a method may also be used is that, at first, as to the amplified product for each dilution series of solution comprising purified DNA sample used as a template, the melting curve is made by plotting the melting temperature of amplification product (double-stranded DNA) as horizontal axis and the first derivation (variation) of fluorescent intensity as vertical axis, and detection of peak is examined. When the Tm value of the peaks of each primer extension product of each dilution series is identical, it can be determined that there is a target mutation in nucleotide sequence in the purified DNA sample.

In addition, as a reference experiment, the real-time PCR is performed by the same method as described above except for using a purified DNA sample derived from the wild type instead of a purified DNA sample purified from a sample to be detected for mutation as a template, and by the same method, the fluorescence intensity emitted by the SYBR™ Green I is measured, and then the melting curve analysis may be performed. In this case, as there is no mutation in nucleotide sequence in the sample, fluorescence could not be detected, and therefore, a peak should not appear in the melting curve analysis. To make the determination of mutation in nucleotide sequence more assured, it is preferable to conduct such a control experiment in parallel.

<Method (1)-2>

Using a Primer c or a Primer d of the present invention, an oligonucleotide primer capable of amplifying a sequence of interest by the nucleic acid amplification reaction in pairs with the above-described primer, and SYBR™ Green I as the intercallator, and using a purified DNA sample purified from a sample to be detected for mutation as a template, real-time PCR is performed using Taq DNA polymerase. And the fluorescent intensity emitted from SYBR™ Green I intercalated into the amplification products is measured.

In order to detect mutation, for example, analysis on the melting curve of amplification products may be performed. That is, the melting curve is made by plotting the melting temperature of amplification product (double-stranded DNA) as horizontal axis and the first derivation (variation) of fluorescent intensity as vertical axis, and detection of peak is examined. When the Tm value of the detected peak of each primer extension product is identical with that of the primer extension product predicted to be amplified by the real-time PCR using the same combination of primers, it can be determined that there is no target mutation in nucleotide sequence in the purified DNA sample. On the other hand, when the Tm value is different, it can be determined that there is a target mutation(s) in nucleotide sequence in the purified DNA sample.

In addition, a method may also be used is that, at first, as to the amplified product for each dilution series of solution comprising purified DNA sample used as a template, the melting curve is made by plotting the melting temperature of amplification product (double-stranded DNA) as horizontal axis and the first derivation (variation) of fluorescent intensity as vertical axis, and detection of peak is examined. When the Tm value of the peak of each primer extension product of each dilution series is identical, it can be determined that there is no target mutation in nucleotide sequence in the purified DNA sample. On the other hand, when the Tm value is different, it can be determined that there is a target mutation(s) in nucleotide sequence in the purified DNA sample.

As an example, a method for detecting mutation in nucleotide sequence by the real-time PCR detection system using intercalator according to the present invention will be explained by taking a case where a single-base mutation in the rpoB gene of human tubercle bacillus is detected using the above-described "Primer rpoB_2" (corresponding to the Primer a of the present invention), (a case where the mutation of base "C" to "T" at the $46^{th}$ from the 5' end in the sequence of a hot spot mutation region in the wild type rpoB gene is detected as described above) (<Method (1)-1>) for instance.

At first, by the known method, the purified DNA sample is obtained from a sample to be detected for a mutation in nucleotide sequence.

In the next place, using the Primer rpoB_2 and an oligonucleotide primer capable of amplifying a sequence of interest by the nucleic acid amplification reaction in pairs with the Primer rpoB_2, for example as described below, the real-time PCR is performed.

That is, 10 mM Tris-HCl buffer solution (pH 8.9) comprising each 50 to 2000 nM of the Primer rpoB_2 and an oligonucleotide primer capable of amplifying a sequence of interest by the nucleic acid amplification reaction in pairs with the Primer rpoB_2, about 5000-1000000 times dilution (final concentration) of the concentrate solution of SYBR™ Green I (trade name of Molecular Probe Inc.), 1.0 to 4.0 mM $MgCl_2$, 80 mM KCl, 500 µg/ml of BSA, 0.1% sodium cholate, 0.005 to 0.2% TritonX-100, 0.2 mM each of dATP, dCTP, dGTP and dTTP, and 10 to 80 U/ml of Taq DNA polymerase is prepared, and used as a reaction solution for PCR. To a 20 µl of the reaction solution for PCR, 1 ng of purified DNA sample purified from a sample to be detected for mutation is added, and used as a DNA sample for PCR. This sample is placed in the well of 96-well reaction plate, and the real-time PCR is performed using appropriate real-time PCR detection equipment and the like. The reaction is repeated for 30 to 50 cycles, and the fluorescent intensity emitted by SYBR™ Green I intercalated into the amplification products is measured at each cycle.

In the next place, the melting curve is made by plotting the melting temperature of amplification product (double-stranded DNA) as horizontal axis and the first derivation (variation) of fluorescent intensity as vertical axis, and detection of peak is examined.

In this case, when the Tm value of the detected peak of the primer extension product is identical with that of the primer extension product predicted to be amplified by the real-time PCR using the same combination of primers, it can be determined that there is a mutation in rpoB gene which is the detection target in the purified DNA sample.

In addition, it may be such a method that when the Tm value of the peak obtained by the melting curve analysis for each primer extension product of each dilution series is identical, it can be determined that there is a mutation in rpoB gene in the purified DNA sample.

In addition, as a reference, either an oligonucreotide comprising rpoB gene of wild type human tubercle bacillus is synthesized by conventional method, or an oligonucreotide comprising rpoB gene is extracted and purified from wild type human tubercle bacillus. And, the real-time PCR is performed by the same method as described above except for using this oligonucleotide instead of "a purified DNA sample purified from a sample to be detected for mutation as a template, and the fluorescence intensity of the SYBR™ Green I is measured by the same way, and then the melting curve analysis may be performed. In this case, as there is no mutation in nucleotide sequence in the sample, fluorescence could not be detected, and therefore, a peak should not appear in the melting curve analysis. To make the determination of mutation in nucleotide sequence more assured, it is preferable to conduct such a control experiment in parallel.

In addition, a method for detecting a single-base mutation in rpoB gene of human tubercle bacillus by the above-described <Method (1)-2> using the Primer c or the Primer d of the present invention includes, for example, the following methods.

That is, using the Primer c or the Primer d of the present invention which are designed based on the above-described hot spot mutation region in rpoB gene of the wild type human tubercle bacillus, an oligonucleotide primer capable of amplifying a sequence of interest by the nucleic acid amplification reaction in pairs with the above-described primer, and the intercallator, and using a purified DNA sample purified from a sample to be detected for a mutation as a template, real-time PCR method by known intecalator method and the following melting curve analysis are performed through the use of known intercalator method by the same method as the above-described <Method (1)-1>.

In this case, when the Tm value of a peak for the primer extension product detected in the melting curve analysis is identical with Tm value of the primer extension product predicted to be amplified by the real-time PCR using the same combination of primers, it can be determined that there is no target mutation in the rpoB gene in the purified DNA sample. On the other hand, when the peaks having the same Tm value cannot be obtained, it can be determined that there is a target mutation(s) in the target rpoB gene in the purified DNA sample.

In addition, it may be such a method that, as a consequence of the melting curve analysis, when the Tm value of the peak obtained for each primer extension product of each dilution series of the purified DNA sample solution is identical, it can be determined that there is no mutation in rpoB gene in the purified DNA sample. On the other hand, when the Tm value of the peaks is different, it can be determined that there is mutation(s) in rpoB gene in the purified DNA sample.

It should be noted that the real-time PCR may be performed using any one kind of Primer a, b, c or d of the present invention, or otherwise, the real-time PCR may be performed by the same method using several kinds of primers of the present invention in the same time. When there exist some sort of mutation in the sample DNA, if only one kind of primer is used, it can be determined only whether the corresponding type of mutation exist or not in the sample DNA. On the other hand, when the several kinds of primers of the present invention are used in the same time, it can be determined whether there exists any of mutation detectable by the several kinds of the applied primers at once, and therefore, this method is extremely effective in the field of clinical laboratory test where swiftness of the determination is required.

The example of the case where the several kinds of primers of the present invention are used includes, for example, a case where several kinds of the Primer a is used, a case where several kinds of the Primer b is used, and a case where (several kinds of) the Primer a and (several kinds of) the Primer b are used appropriately in combination.

For example, when a mutation in rpoB gene of tubercle bacillus is detected, if the real-time PCR is performed using only the Primer rpoB_2, it can be determined only whether the mutation detectable by the Primer rpoB_2 exist or not, namely only whether the mutation of base "C" at the $46^{th}$ to "T" exists or not in the sequence of a hot spot mutation region in the wild type rpoB gene, and if there exist another mutation, the existence of such mutation can not be determined. On the other hand, for example, if the real-time PCR is performed using the Primer rpoB_2, the Primer rpoB_2_n3, the Primer rpoB_6 and the Primer rpoB_3 together in the same time, and if there exist any of a mutation of base "C" at the $46^{th}$ to "T", a mutation of base "T" at the $68^{th}$ to "C", a mutation of base "C" at the $46^{th}$ to "G", a mutation of base "A" at the $47^{th}$ to "T", a peak can be obtained by the melting curve analysis, and thereby it can be determined that there are some sort of mutation among the above-described four kinds of mutations in rpoB gene of the sample. In addition, by analyzing the position where peaks appear, it can be determined specifically which mutation among four types of mutations exists.

(2) TaqMan™ Real-Time PCR Method

In the method for detecting mutation(s) in nucleotide sequence of the present invention, TaqMan™ real-time amplification detection method (see, for example, the documents in U.S. Pat. No. 5,210,015 and U.S. Pat. No. 5,538,848) may also be used.

The TaqMan™ real-time amplification detection method (TaqMan™ real-time PCR method) is, in more specifically, the method capable of detecting target of small amount of target DNA quantitatively with high sensitivity by the real-time PCR method using a probe in which the 5'end thereof is labeled with a fluorescent dye (reporter) such as FAM, and the 3'end thereof is labeled, for example with a quencher dye such as TAMRA (see, for example, the document in U.S. Pat. No. 5,538,848).

The principle of the TaqMan™ real-time PCR method is explained as follows:

That is, an oligonucleotide probe, which the 5'end thereof is labeled with a fluorescent dye (reporter) and the 3'end thereof is labeled with a quencher dye, and capable of hybridizing with a specific region in the target gene, is used. In the above-described probe, the fluorescence of the reporter is suppressed by the quencher dye under normal condition. In a state where this fluorescent probe is hybridized completely with the target gene, PCR is performed from the outside thereof using DNA polymerase. According to the progression of the extension reaction by DNA polymerase, the fluorescent probe is hydrolyzed from the 5'end by its exonuclease activity, and the released reporter dye generates fluorescence. In the TaqMan™ real-time PCR method, by monitoring the intensity of this fluorescence in real time, the initial amount of the template DNA can be quantified accurately.

As a probe to be used for the probe labeled with a fluorescent dye (reporter) at the 5'end thereof and with a quencher dye at the 3'end thereof to be used for the TaqMan™ real-time PCR detection method of the present invention, a probe having a nucleotide sequence of primer extension product obtained (predicted to be amplified) when the real-time PCR is performed by the combinational use of the selected forward primer and a reverse primer, or a probe having a nucleotide sequence designed further from such sequence may be used.

In addition, the reporter fluorescent substance for labeling the 5' end includes carboxyfluorescein (FAM), hexachlorofluorescein (HEX), tetrachlorofluorescein (TET), Cy5 (Amersham Biosciences K.K.) and the like, however, FAM is preferable among them. The quencher dye for labeling its 3'end includes fluorescent substance such as carboxytetramethylrhodamine (TAMRA), nonfluorescent substance such as Black Hole Quencher dye (for example, BHQ2), 4-((4-(dimethylamino)phenyl)azo)benzoic acid (DABCYL), and TAMRA is preferable among them.

Other reagents to be used for the TaqMan™ real-time PCR method such as deoxyribonucleoside 3-phosphate (dATP, dCTP, dGTP, dTTP) and DNA polymerase to be used the same reagents as usually used in the conventional real-time PCR. The procedure of the TaqMan™ real-time PCR may be performed according to the customary protocol of the TaqMan™ real-time PCR except for the use of the primer and the probe of the present invention.

The example of "the method for detecting mutation(s) in nucleotide sequence by the TaqMan™ real-time PCR method" of the present invention would be explained as follows:

<Method (2)-1>

The Primer a or the Primer b of the present invention and an oligonucleotide primer capable of amplifying a sequence of interest by the nucleic acid amplification reaction in pairs with the above-described primer are used. And besides, based on the nucleotide sequence of the primer extension product predicted to be amplified by PCR using the combination of the above-described primers, an oligonucleotide with appropriate length is designed and synthesized by a conventional method. Using the oligonucleotide which is labeled with a reporter dye on its 5'end and labeled with a quencher dye on its 3'end as a labeled probe, and using a purified DNA sample purified from a sample to be detected for mutation as a template, the TaqMan™ real-time PCR is performed. When a fluorescence derived from the reporter dye is measured, it can be determined that there is a target mutation in nucleotide sequence in the purified DNA sample.

When the <Method (2)-1> is practiced, as the similar method in the intercalator method, it is preferable to conduct a control experiment using purified DNA derived from the wild type as a template in parallel.

<Method (2)-2>

The Primer c or the Primer d of the present invention and an oligonucleotide primer capable of amplifying a sequence of interest by the nucleic acid amplification reaction in pairs with the above-described primer are used. And besides, based on the nucleotide sequence of the primer extension product predicted to be amplified by PCR using the combination of the above-described primers, an oligonucleotide with appropriate length is designed and synthesized by a conventional method. Using the oligonucleotide which is labeled with a reporter dye on its 5'end with a quencher dye on its 3'end as a labeled probe, and using a purified DNA sample purified from a sample to be detected for a mutation as a template, the TaqMan™ real-time PCR is performed. When a fluorescence derived from the reporter dye is measured, it can be determined that there is no target mutation in nucleotide sequence in the purified DNA sample. On the other hand, when fluorescence derived from the reporter dye is not measured, it can be determined that there is a target mutation in nucleotide sequence in the purified DNA sample.

The plural number of mutation may be determined at the same time by conducting the TaqMan™ real-time PCR using several kinds of primers of the present invention. And, this is the same situation as the case where the determination is performed by the above-described intercalation method.

As an example, a method for detecting mutation in nucleotide sequence by the TaqMan™ real-time PCR detection method of the present invention will be explained by taking a case where a single-base mutation in the rpoB gene of human tubercle bacillus is detected using the above-described "Primer rpoB_2" (as described above, a case where the mutation of base "C" to "T" at the 46$^{th}$ from the 5'end in the sequence of a hot spot mutation region in the wild type rpoB gene is detected) (<Method (2)-1>) for instance as follows.

At first, the purified DNA sample is obtained from a sample to be detected for a mutation in nucleotide sequence by the known method.

In the next place, based on the nucleotide sequence of the primer extension product predicted to be amplified by the PCR using the combination of the Primer rpoB_2 and an oligonucleotide primer capable of amplifying a sequence of interest by the nucleic acid amplification reaction in pairs with the Primer rpoB_2, an oligonucleotide with appropriate length is designed and synthesized by a conventional method. The 5'end of this oligonucleotide is bound with a reporter dye of FAM and the 3'end thereof is bound with a quencher dye (reporter quenching agent) of TAMRA by the conventional method, and thus a labeled probe is obtained.

In the next place, using the Primer rpoB_2, an oligonucleotide primer capable of amplifying a sequence of interest by the nucleic acid amplification reaction in pairs with the Primer rpoB_2, and a labeled probe obtained above, the TaqMan™ real-time PCR is performed, for example, as described below:

That is, 10 mM Tris-HCl buffer solution (pH 8.9) comprising each 1 µM of the Primer rpoB_2 and an oligonucleotide primer capable of amplifying a sequence of interest by the nucleic acid amplification reaction in pairs with the Primer rpoB_2, 100 to 1000 nM the labeled probe, 1.0 to 4.0 mM MgCl$_2$, 80 mM KCl, 500 µg/ml of BSA, 0.1% sodium cholate, 0.005 to 0.2% TritonX-100, 0.2 mM each of dATP, dCTP, dGTP and dTTP, and 10 to 80 U/ml of Taq DNA polymerase is prepared, and used as a reaction solution for PCR. To a 20 µl of above-described reaction solution for PCR, 1 ng of purified DNA sample purified from a sample to be detected for mutation is added, and used as a DNA sample for PCR. This sample is placed in the well of 96-well reaction plate, and the real-time PCR is performed using appropriate real-time PCR detection equipment and the like. The reaction is repeated for 30 to 50 cycles, and the fluorescence intensity derived from the reporter dye is measured at each cycle.

In this case, when the fluorescence derived from the reporter dye is measured, it can be determined that there is a mutation in the target rpoB gene in the purified DNA sample.

In addition, as described above, it is preferable to conduct a control experiment using purified DNA comprising rpoB gene of wild type human tubercle bacillus as a template in parallel.

A method for detecting single base mutation in rpoB gene of human tubercle bacillus by the above-described <Method (2)-2> using the Primer c or the Primer d of the present invention includes, for example, the following methods:

That is, using the Primer c or the Primer d of the present invention which are designed based on the above-described hot spot mutation region in rpoB gene of the wild type human tubercle bacillus, an oligonucleotide primer capable of amplifying a sequence of interest by the nucleic acid amplification reaction in pairs with the above-described primer, and a labeled probe prepared by the same method as described in <Method (2)-1>, the TaqMan™ real-time PCR is performed by the same method as above-described <Method (2)-1>.

In this case, when the fluorescence derived from the reporter dye is measured, it can be determined that there is no mutation in the target rpoB gene in the purified DNA sample. On the other hand, when the fluorescence is not measured, it can be determined that there is a mutation in the target rpoB gene in the purified DNA sample.

In addition, present invention can be applied in the nucleic acid amplification process with a detection method using RNA replication product. For example, NASBA (nucleic acid sequence based amplification) method (Japanese Patent No. 2650159), 3SR (self-sustained sequence replication) method (JP-B-Hei 7-114718), TAS (transcription based amplification system) method (JP-A-Hei 2-500565; International Publication No. WO88/10315), and TMA (transcription mediated amplification) method (JP-A-1999-46778) are included, however, among them, isothermal nucleic acid amplification method utilizing concerted reaction of reverse transcriptase and RNA polymerase (a reaction is perfumed under the condition where reverse transcriptase and RNA polymerase act concertedly) is suitable for the automation of the determination system.

(3) A Method in which, after the Nucleic Acid Amplification Reaction is Performed, the Primer Extension Products Obtained are Subjected to Electrophoresis This method includes, for example, "the method for detecting mutation(s) in nucleotide sequence comprising, the following steps of:

(i) performing a nucleic acid amplification reaction (PCR) by using a primer selected from the Primer a, the Primer b, the Primer c or the Primer d of the present invention, and an oligonucleotide primer capable of amplifying a sequence of interest by nucleic acid amplification reaction in pairs with the above-described primer, and using the nucleic acid in a sample as a template, (ii) electrophoresing the primer extension product obtained in the above (i), and detecting mutation(s) in nucleotide sequence is detected on the basis of the obtained result.".

A method for detecting mutation(s) in nucleotide sequence based on the results of electrophoresis includes, for example, (3-1) the method for detection by confirming a fraction of primer extension product having objective size (number of base pair);

(3-2) the method for detection by hybridization using labeled probe.

Condition and operation procedure of the electrophoresis may be according to the conventional method usually performed in this field.

(3-1) The Method for Detection by Confirming a Fraction of Primer Extension Product Having Objective Size (Number of Base Pair)

As to the method for detection by confirming a fraction of primer extension product having objective size (number of base pair), for example, first of all, PCR is performed, and then the primer extension product obtained is subjected to electrophoresis. The size (number of base pair) of the primer extension product predicted to be amplified by PCR using the combination of the primers of the present invention and an oligonucleotide primer capable of amplifying a sequence of interest by the nucleic acid amplification reaction in a pair with the above-described primer is estimated in advance. And, the confirmation whether the size of the fraction obtained is relevant to the size of the predicted amplification product may be performed by the conventional method. For example, the method in which, in such a method that the obtained fraction is visualized by staining with ethidium bromide and the like, the amplification product is detected (confirmed) based on the characteristic size thereof is included.

The example of "the method for detection by confirming the fraction of the primer extension product having objective size (number of base pair)" of the present invention would be explained as follows:

<Method (3-1)-1>

The Primer a or the Primer b of the present invention and an oligonucleotide primer capable of amplifying a sequence of interest by the nucleic acid amplification reaction in pairs with the above-described primer are selected. Further, the size (number of base pair) of the primer extension product predicted to be amplified by the PCR using this combination of the primers is estimated in advance. Using the combination of the above-described primers, and using a purified DNA sample purified from a sample to be detected for a mutation as a template, PCR is performed, and then the primer extension product obtained is subjected to electrophoresis. In the next place, the confirmation whether the size of the fraction obtained is relevant to the size of the predicted amplification product may be performed by the conventional method. For example, in such a method that the obtained fraction is visualized by staining with ethidium bromide and the like, the amplification product is detected by the characteristic size thereof, and when the size of the fraction obtained is confirmed to correspond to the size of the predicted amplification product, it can be determined that there is target mutation in nucleotide sequence in the purified DNA sample.

<Method (3-1)-2>

The Primer c or the Primer d of the present invention, and an oligonucleotide primer capable of amplifying a sequence of interest by the nucleic acid amplification reaction in pairs with the above-described primer is selected. Further, the size (number of base pair) of the primer extension product predicted to be amplified by the PCR using this combination of the primers is estimated in advance. Using the combination of the above-described primers, and using a purified DNA sample purified from a sample to be detected for mutation as a template, PCR is performed, and then the primer extension product obtained is subjected to electrophoresis. In the next place, the confirmation whether the size of the fraction obtained is relevant to the size of the predicted amplification product may be performed by the conventional method. For example, in such a method that the obtained fraction is visualized by staining with ethidium bromide and the like, the amplification product is detected by the characteristic size thereof, and when the size of the fraction obtained is confirmed to correspond to the size of the predicted amplification product, it can be determined that there is no target mutation in nucleotide sequence in the purified DNA sample. On the other hand, when such fraction is not confirmed, it can be determined that there is target mutation in nucleotide sequence in the purified DNA sample.

The plural number of mutation may be determined at the same time by conducting PCR and electrophoresis as described above using several kinds of primers of the present invention. And, this is the same situation as the case where the determination is performed by the above-described intercalation method.

As an example, a method for detecting mutation in nucleotide sequence by the method of (3-1) for the present invention will be explained by taking a case where a single-base mutation in the rpoB gene of human tubercle bacillus is detected using the above-described "Primer rpoB_2" (as described above, a case where the mutation of base "C" to "T" at the $46^{th}$ from the 5'end in the sequence of a hot spot mutation region in the wild type rpoB gene is detected) (<Method (3-1)-1>) for instance as follows.

At first, the purified DNA sample is obtained from a sample to be detected for a mutation in nucleotide sequence by the known method.

In the next place, using the Primer rpoB_2 and an oligonucleotide primer capable of amplifying a sequence of interest by the nucleic acid amplification reaction in pairs with the Primer rpoB_2, and using a purified DNA sample purified from a sample to be detected for a mutation as a template, PCR is performed. Then, the obtained primer extension product is subjected to electrophoresis. The size (number of base pair) of the amplification product predicted to be amplified by PCR using this combination of primers is estimated in advance. The confirmation whether the size of the fraction obtained is relevant to that of the predicted amplification product may be performed by conventional method. When the size of the fraction obtained is confirmed to correspond to the size of the predicted amplification product, it can be determined that there is a mutation in the target rpoB gene in the purified DNA sample.

In addition, a method for detecting single-base mutation in rpoB gene of human tubercle bacillus by the above-described <Method (3-1)-2> using the Primer c or the Primer d of the present invention includes, for example, the following methods.

That is, using the Primer c or the Primer d which are designed based on the above-described hot spot mutation region in rpoB gene of the wild type human tubercle bacillus and an oligonucleotide primer capable of amplifying a sequence of interest by nucleic acid amplification reaction in pairs with the above-described primer, and using a purified DNA sample purified from a sample to be detected for mutation as a template, PCR is performed by the same method as above-described <Method (3-1)-1>. Then, the primer extension product obtained is subjected to electrophoresis. The size (number of base pair) of the amplification product predicted to be amplified by the PCR using this combination of the primers is estimated in advance. The confirmation whether the size of the fraction obtained is relevant to the size of the predicted amplification product may be performed by the conventional method. When the size of the fraction obtained is confirmed to correspond to the size of the predicted amplification product, it can be determined that there is no mutation in the target rpoB gene in the purified DNA sample. On the other hand, when such fraction is not confirmed, it can be determined that there is a mutation in the target rpoB gene in the purified DNA sample.

(3-2) The Method for Determination by Hybridization Using Labeled Probe.

As to the method for determination by hybridization using labeled probe, for example, the following methods are included. At first, PCR amplification product is subjected to the electrophoresis. In the next place, an oligonucleotide, which comprises a sequence to be detected and labeled with a labeling substance, is used as a labeled probe; the obtained fraction is subjected to hybridization with the above-described labeled probe. Then, by detecting signal from the above-described labeled probe, the existence or nonexistence of the hybridized fraction with the above-described labeled probe is confirmed, and the existence of mutation in nucleotide sequence is detected.

The "oligonucleotide which comprises a sequence to be detected" used in the above-described method includes an oligonucleotide having the same nucleotide sequence as a nucleotide sequence of an amplification product predicted to be amplified by PCR using the combination of the primer, or an oligonucleotide further designed from the sequence and having an appropriate length.

The specific example of labeling substance with which the probe to be used for the above-described method, and the method for labeling the probe are the same labeling substance and the same labeling method as used for the above-described labeled primer.

The example of "the method for determination by hybridization using labeled probe" of the present invention would be explained as follows:

<Method (3-2)-1>

PCR is performed by using the Primer a or the Primer b of the present invention, and an oligonucleotide primer capable of amplifying a sequence of interest by nucleic acid amplification reaction in pairs with the above-described primer, and using a purified DNA sample purified from a sample to be detected for a mutation as a template, PCR is performed. Then, the primer extension product obtained is subjected to electrophoresis. The labeled probe is prepared in advance by labeling an oligonucleotide comprising a sequence to be detected with a labeling substance. The obtained fraction is subjected to hybridization with the above-described labeled probe. The signal from the labeled probe is examined, and when a fraction hybridized with the above-described labeled probe is confirmed, it can be determined that there is a target mutation in nucleotide sequence in the purified DNA sample.

<Method (3-2)-2>

PCR is performed by using the Primer c or the Primer d of the present invention, and an oligonucleotide primer capable of amplifying a sequence of interest by nucleic acid amplification reaction in pairs with the above-described primer, and using a purified DNA sample purified from a sample to be detected for a mutation as a template, PCR is performed. Then, the primer extension product obtained is subjected to electrophoresis. The labeled probe is prepared in advance by labeling an oligonucleotide comprising a sequence to be detected with a labeling substance. The obtained fraction is subjected to hybridization with the above-described labeled probe. The signal from the labeled probe is examined, and when a fraction hybridized with the above-described labeled probe is confirmed, it can be determined that there is no target mutation in nucleotide sequence in the purified DNA sample. On the other hand, when such fraction is not confirmed, it can be determined that there is a target mutation in nucleotide sequence in the purified DNA sample.

The plural number of mutation may be determined at the same time by conducting PCR and electrophoresis as described above using several kinds of primers of the present invention. And, this is the same situation as the case where the determination is performed by the above-described intercalation method.

As an example, a method for detecting mutation(s) in nucleotide sequence by the method of (3-2) of the present invention will be explained by taking a case where a single-base mutation in the rpoB gene of human tubercle bacillus is detected by using the above-described "Primer rpoB_2" (as described above, a case where the mutation of base "C" to "T" at the $46^{th}$ from the 5' end in the sequence of a hot spot mutation region in the wild type rpoB gene is detected) (<Method (3-2)-1>) for instance as follows.

At first, the purified DNA sample is obtained from a sample to be detected for a mutation in nucleotide sequence by the known method.

In the next place, using the Primer rpoB_2 and an oligonucleotide primer capable of amplifying a sequence of interest by the nucleic acid amplification reaction in pairs with the Primer rpoB_2, and using a purified DNA sample purified from a sample to be detected for mutation as a template, PCR is performed. Then, the obtained primer extension product is subjected to electrophoresis. Based on the nucleotide sequence of the amplification product predicted to be amplified by PCR using this combination of primers, a sequence having an appropriate length for use in a probe is designed, and an oligonucleotide with this sequence is synthesized by the conventional method in advance. The labeled probe is also prepared in advance by labeling this oligonucleotide with a labeling substance. The obtained fraction is subjected to hybridization with the above-described labeled probe. When a fraction hybridized with the above-described labeled probe is confirmed by detecting a signal from the labeled probe, it can be determined that there is a target mutation in rpoB gene in the purified DNA sample.

In addition, a method for detecting single-base mutation in rpoB gene of human tubercle bacillus by the above-described <Method (3-2)-2> using the Primer c or the Primer d of the present invention includes, for example, the following methods.

That is, using the Primer c or the Primer d which are designed based on the above-described hot spot mutation region in rpoB gene of the wild type human tubercle bacillus, an oligonucleotide primer capable of amplifying a sequence of interest by nucleic acid amplification reaction in pairs with the above-described primer, and using a purified DNA sample purified from a sample to be detected for a mutation as a template, PCR and subsequently the electrophoresis are carried out by the same method as above-described <Method (3-2)-1>. Based on the nucleotide sequence of the amplification product predicted to be amplified by PCR using this combination of primers, a sequence having an appropriate length for use in a probe is designed, and an oligonucleotide with this sequence is synthesized by the conventional method in advance. The labeled probe is also prepared in advance by labeling this oligonucleotide with a labeling substance. The obtained fraction is subjected to hybridization with the above-described labeled probe. When a fraction hybridized with the above-described labeled probe is confirmed by detecting a signal from the labeled probe, it can be determined that there is no target mutation in rpoB gene in the purified DNA sample. On the other hand, when such fraction is not confirmed, it can be determined that there is a target mutation in rpoB gene in the purified DNA sample.

(4) A Method for Measuring the Signal of the Primer Extension Product Obtained by the Nucleic Acid Amplification Reaction Using a Labeled Primer This method includes a method comprising using a labeled primer prepared from the primer of the present invention by the above-described labeling method and an oligonucleotide primer (it is not labeled.) capable of amplifying a sequence of interest by nucleic acid amplification reaction in pairs with the above-described primer, and using the nucleic acid in a sample as a template, performing PCR, and then measuring the signal of the obtained primer extension product.

The example would be explained as follows:

<Method (4)-1>

PCR is performed by using the labeled Primer a or the labeled Primer b, an oligonucleotide primer (it is not labeled.) capable of nucleic acid amplification reaction in pairs with the above-described primer, and using a purified DNA sample purified from a sample to be detected for a mutation as a template. After that, the free-labeled primer is removed, and then the signal from the primer extension product is measured. When the signal is detected, it can be determined that there is a target mutation in nucleotide sequence in the purified DNA sample.

<Method (4)-1>

PCR is performed by using the labeled Primer c or the labeled Primer d, an oligonucleotide primer (it is not labeled.) capable of nucleic acid amplification reaction in pairs with the above-described primer, and using a purified DNA sample purified from a sample to be detected for a mutation as a template. After that, the free-labeled primer is removed, and then the signal from the primer extension product is measured. When the signal is detected, it can be determined that there is no target mutation in nucleotide sequence in the purified DNA sample. On the other hand, when the signal is not detected, it can be determined that there is a target mutation in nucleotide sequence in the purified DNA sample.

In the above-described method, the method of removing the free labeled primer includes a method in which after the primer extension product in the reaction mixture obtained by PCR is precipitated by the conventional nucleic acid precipitation method (ethanol precipitation method, a method of the precipitation using isopropanol, and the like), the supernatant solution containing the not-precipitated free labeled primer is removed, and the like.

In addition, the method of separating the primer extension product from the free labeled primer by treating the reaction products obtained by PCR with gel chromatography under appropriate condition, or a electrophoretic separation method, and the like are also included.

It should be noted that, as the reagents to be used in the method for detecting mutation(s) in nucleotide sequence of the present invention, the reagents which are usually used in this field such as, for example, buffering agents, stabilizers and preservatives, and which do not inhibit the stability of coexisting reagents and the like, and does not inhibit PCR and the hybridization reaction, may be utilized. Also, the concentration of the reagent may be selected appropriately from the range of concentration usually used in this field.

Specific example of buffer solution includes, all the buffer solutions customarily used when the conventional PCR and the hybridization reaction are performed, for example, Tris buffer, phosphate buffer, veronal buffer, borate buffer and Good's buffer, and the pH thereof is not specifically limited, but normally the pH range of 5 to 9 is preferable.

In addition, as need arises, a nucleic acid synthesizing enzyme (DNA polymerase, RNA polymerase, reverse transcriptase and the like), a substrate appropriate for the enzyme (dNTP, rNTP and the like), and also, a double strand intercalator (ethidium bromide, SYBR™ Green and the like) or a signal detection substance such as FMA and TAMRA and the like may be used.

A kit for detecting mutation(s) in nucleotide sequence of the present invention includes "a kit for detecting mutation(s) in nucleotide sequence, comprising any one of oligonucleotide described in the following (a)-(d) or a salt thereof as a primer:

(a) an oligonucleotide, i) wherein the oligonucleotide has the same nucleotide as a mutant nucleotide in a target gene at the 3'end position thereof, ii) wherein the oligonucleotide has the same nucleotide sequence as a nucleotide sequence of the target gene except for its 3'end position, and has the same nucleotide sequence as the nucleotide sequence of the target gene toward the 5'-side from the position where the mutant nucleotide may exist in the target gene, and iii) wherein the nucleotide at the second position from the 3'end thereof has a modification capable of inhibiting a reaction of nucleic acid synthesis, or a salt thereof;

(b) an oligonucleotide, i) wherein the oligonucleotide has a nucleotide complementary to a mutant nucleotide in a target gene at the 3'end position thereof, ii) wherein the oligonucleotide has a nucleotide sequence complementary to a nucleotide sequence of the target gene except for its 3'end position, and has a nucleotide sequence complementary to the nucleotide sequence of the target gene toward the 3'-side from a position where the mutant nucleotide may exist in the target gene, and iii) wherein the nucleotide at the second position from the 3'end thereof has a modification capable of inhibiting a reaction of nucleic acid synthesis, or a salt thereof;

(c) an oligonucleotide, i) wherein the oligonucleotide has the same nucleotide as a reference nucleotide in a target gene at the 3'end position thereof, ii) wherein the oligonucleotide has the same sequence as a nucleotide sequence of the target gene except for its 3'end position, and has the same nucleotide sequence as the nucleotide sequence of the target gene toward the 5'-side from a position where the reference nucleotide exist in the target gene, and iii) wherein the nucleotide at the second position from the 3'end thereof has a modification capable of inhibiting a reaction of nucleic acid synthesis,
or a salt thereof;
(d) an oligonucleotide,
   i) wherein the oligonucleotide has a nucleotide complementary to a reference nucleotide in a target gene at the 3'end position thereof,
   ii) wherein the oligonucleotide has a nucleotide sequence complementary to a nucleotide sequence of the target gene except for its 3'end position, and has a nucleotide sequence complementary to the nucleotide sequence of the target gene toward the 3'-side from a position where the reference nucleotide exist in the target gene, and
   iii) wherein the nucleotide at the second position from the 3' end thereof has a modification capable of inhibiting a reaction of nucleic acid synthesis,
or a salt thereof.

The preferable aspect and the specific example of the constitutive reagents composing these kits are as described above.

In addition, the above-described kit further includes a kit comprising "1) nucleoside 3-phosphate, 2) nucleic acid synthesizing enzyme, 3) an oligonucleotide capable of amplifying a sequence of interest by the nucleic acid amplification reaction in pairs with above-described oligonucleotide, and 4) PCR buffer solution".

The nucleic acid synthesizing enzyme of the above-described 2) includes, for example, DNA polymerase, RNA polymerase and reverse transcriptase.

The specific example of buffer solution to be used for PCR buffer solution of the above-described 4) includes, all the buffer solutions customarily used when the conventional PCR and the hybridization reaction are performed, for example, Tris buffer, phosphate buffer, veronal buffer, borate buffer and Good's buffer, and the pH thereof is also not specifically limited, but normally the pH range of 5 to 9 is preferable.

In addition, the kit for detecting mutation(s) in nucleotide sequence of the present invention may comprise, as need arises, a substrate appropriate for the enzyme (dNTP, rNTP and the like), and also for example, a double strand intercalator such as SYBR™ Green I (trade name of Molecular Probes Inc.), ethidium bromide, fluorene, a signal detection substance such as FAM and TAMRA. In addition, the reagent which is usually used in this field such as, for example, stabilizers and preservatives, and which does not inhibit the stability of coexisting reagents and the like, and does not inhibit PCR and the hybridization reaction, may be comprised. Also, the concentration of the reagent may be selected appropriately from the range of concentration usually used in this field.

The material to be used for the method for detecting nucleotide sequence of the present invention includes biological samples obtained from test subject such as plasma, serum, cerebrospinal fluid, component extraction solutions from various body tissues, tissue sections, fecal matter, and urine. In addition, cells derived from above-described various tissues are also included.

For example, the material to be used for the method for detecting mutation(s) of human tubercle bacillus includes various clinical specimens such as expectorate sputum, transbronchial specimen, pharyngeal mucus, gastric fluid, puncture fluid such as bronchial washing solution, pleural effusion, and the like.

The sample to be used for the method for detecting mutation(s) in nucleotide sequence of the present invention includes the sample comprising nucleic acid. It may be the nucleic acid isolated and purified from the above-described materials, or may be the nucleic acid amplified by the nucleic acid amplification and detection system and the like.

The present invention will be described in more detail by way of example thereof. It should be noted, however, that the present invention should not be limited thereto.

It should be noted that, in the example and the comparative example, "A" shown as a nucleic acid base represents adenine, "G" represents guanine, "C" represent cytosine, and "T" represents thymine respectively.

EXAMPLES

Example 1

Detection of Drug Resistant Tubercle Bacillus:
Model Experiment 1

(1) Construction of Plasmid DNA
1) Construction of Plasmid DNA Comprising Mutant Type rpoB Gene Sequence_2

Referring to "the sequence of a hot spot mutation region in rpoB gene" reported by VIVEK KAPUR et al. (Non-patent Document 2: J. Clin. Microbiol., vol. 32, No. 4, 1994. p 1095-1098, FIG. 1), a "plasmid DNA having a sequence with a single-base mutation in rpoB gene of tubercle bacillus" was prepared by gene engineering. It should be noted that this sequence of a hot spot mutation region in rpoB gene is identical between human tubercle bacillus (*Mycobacterium tuberculosis*) and bovine tubercle bacillus (*Mycobacterium bovis*).

First, using genomic DNA extracted and purified from *Mycobacterium bovis* BCG (bovine tubercle *bacillus, Strain No. RIMD*1314006, Japanese Society for Bacteriology) as a starting material, and according to the known method of introducing site-directed mutagenesis by PCR described in "Toru Komano ed. Seibutsukagaku Jikkenhou vol. 47; A manual of PCR experiments", introduction of mutation into a base at the $46^{th}$ from the 5' end of the sequence (SEQ ID NO: 1) of a hot spot mutation region in rpoB gene in the genomic DNA of the tubercle bacillus to "T" was performed, while it should be "C" in the wild type.

The mutation-introduced DNA fragment was purified using a column produced by QIAGEN K.K., and then inserted into a cloning vector (produced by Invitrogen Corporation). After that, using QIAprep™ Spin Miniprep Kit (produced by QIAGEN K.K.), the plasmid DNA comprising objective sequence was purified and recovered.

The plasmid DNA obtained by the above-described method comprises a nucleotide sequence shown in SEQ ID NO:3 described below. This nucleotide sequence shown in SEQ ID NO:3 is hereinafter described as "mutant type rpoB gene sequence_2". In the sequence of the "mutant type rpoB gene sequence 2", the underlined base at the $64^{th}$ from the 5'end thereof corresponds to the base at the $46^{th}$ from the 5'end in a hot spot mutation region in rpo B gene. And, a base at this position in the wild type rpo B gene is "C", but is substituted into "T" in the "mutant type rpoB gene sequence_2".

SEQ ID NO:3:
5'-TTCTTCGGCACCAGCCAGCTGAGCCAATTCATGGACCAGAACAACCC

GCTGTCGGGGTTGACC<u>T</u>ACAAGCGCCGACTGTCGGCGCTGGGG-3'

(mutant type rpoB gene sequence_2)

2) Construction of Plasmid DNA Comprising Wild Type rpoB Gene Sequence

The plasmid DNA comprising wild type rpoB gene sequence was obtained by the same method as described above except for not introducing base mutation. That is, this plasmid DNA comprises a nucleotide sequence shown in the following SEQ ID NO:2.

```
SEQ ID NO:2:
5'-TTCTTCGGCACCAGCCAGCTGAGCCAATTCATGGACCAGAACAACCC

GCTGTCGGGGTTGACCCACAAGCGCCGACTGTCGGCGCTGGGG-3'
```

(2) Construction of a Primer (Primer rpoB_2) for Detection of Mutant Type rpoB Gene Based on the mutant type rpoB gene sequence_2, the primer was designed by the following method.

First, the primer sequence for the detection of the mutant type rpoB gene was designed so that (i) the position to be introduced with a mutation in the mutant type rpoB gene sequence_2, namely, the base "T" at the 64$^{th}$ from the 5'end thereof, will be set at the 3'end of the primer, (ii) the other sequence of the primer will be set to be identical to the nucleotide sequence with 16 bases toward the 5'-side from the base "T" at the 64$^{th}$ from the 5'end in the mutant type rpoB gene sequence_2, and moreover (iii) the base "C" at the second position from the 3'end of the primer will substituted with the "C" which is modified with 2'-O,4'-C-Ethylene-bridged Nucleic Acids. The oligonucleotide designed in this method is described as "Primer rpoB_2". The nucleotide sequence of the "Primer rpoB_2" is shown in the following SEQ ID NO:7.

That is, in the nucleotide sequence shown in the SEQ ID NO:7 described below, the underlined nucleotide at the 3'end is the position where the "C" in the wild type is substituted into "T". In addition, the base "C" at the second position from the 3'end is the "C" which is modified with 2'-O,4'-C-Ethylene-bridged Nucleic Acids.

```
SEQ ID NO:7: 5'-GCTGTCGGGGTTGACCT-3'
```

The designed "Primer rpoB_2" was obtained through the use of custom service of Sigma Genosys.

(3) Detection of the Mutant Type rpoB Gene by the Real-Time PCR Detection and Determination of the Effects from False Positive Reactions 1) Preparation of DNA Sample for PCR By measuring absorbance of the plasmid DNA sample comprising the mutant type rpoB gene sequence_2 obtained in the above-described (1), the amount of DNA in the plasmid DNA sample was measured. In the next place, the plasmid DNA sample was diluted using 10 mM Tris-HCl buffer (pH 8.9) to prepare a dilution series of $10^5$, $10^4$, $10^3$, and $10^2$ copies/µl, and used them as DNA samples for PCR.

2) Preparation of the Reaction Solution for PCR

A 10 mM Tris-HCl (pH 8.9) containing each 300 nM of the Primer rpoB_2 obtained in the above-described (2) and a universal primer (M13-forward primer, Takara Bio Inc.), a 30 times dilution (30000 times dilution in final) of the original concentration of SYBR™ Green I (trade name of Molecular Probes Inc.) as a intercalating dye, 1.5 mM $MgCl_2$, 80 mM KCl, 500 µg/ml of BSA, 0.1% sodium cholate, 0.1% TritonX-100, 0.2 mM each of dATP, dCTP, dGTP and dTTP, and 40 U/ml of Taq DNA polymerase (produced by Nippon Gene Co., Ltd.) was prepared, and used the solution as a reaction solution for PCR.

It should be noted that, in this time, as a partner primer to be combined with the Primer rpoB_2, M13-forward primer was used; and the reason for this combination was because in this case the employed DNA sample for PCR was a plasmid DNA comprising the mutant type rpoB gene sequence_2 (hereinafter, the same as above).

3) Real-Time PCR

Using a plasmid DNA comprising the mutant type rpoB gene sequence_2 prepared in the above-described (1) 1) as a template DNA (an amplification target), real-time PCR was performed. In addition, by the method described below, the quantitative monitoring by intercalation method was performed, and the results of real-time PCR were studied and evaluated.

That is, 1 µl of each dilution series of the DNA sample for PCR prepared in the above-described (3) 1) and 19 µl of the reaction solution for PCR prepared in the above-described (3) 2) were placed in a well of a 96-well reaction plate (Micro-Amp Optical 96-Well Reaction Plate, produced by Applied Biosystems Japan), and the real-time PCR was performed using personal thermal cycler and detection system for Taq-Man™ PCR (ABI 7500, produced by Applied Biosystems Japan). Namely, after the reaction solution was heated at 95° C. for 10 minutes, a reaction cycle consisting a reaction at 95° C. for 15 seconds and a reaction at 60° C. for 1 minute was repeated for 40 cycles. After that, the fluorescent intensity emitted from SYBR™ Green I corresponding to the amplification products was measured.

In addition, using a plasmid DNA comprising the wild type rpoB gene sequence prepared in the above-described (1) 2) as a template DNA, and by the same method as above-described (3) except for the use of above-described plasmid DNA, the preparation of DNA sample for PCR, the preparation of the reaction solution for PCR and the real-time PCR were performed.

(4) Melting Curve Analysis

The melting curve was made for each amplification product for the dilution series of the DNA sample for PCR by plotting the melting temperature of amplification product (double-stranded DNA) as horizontal axis and the first derivation (variation) of fluorescent intensity as vertical axis, and detection of peak was examined.

(5) Results

Figure 2:
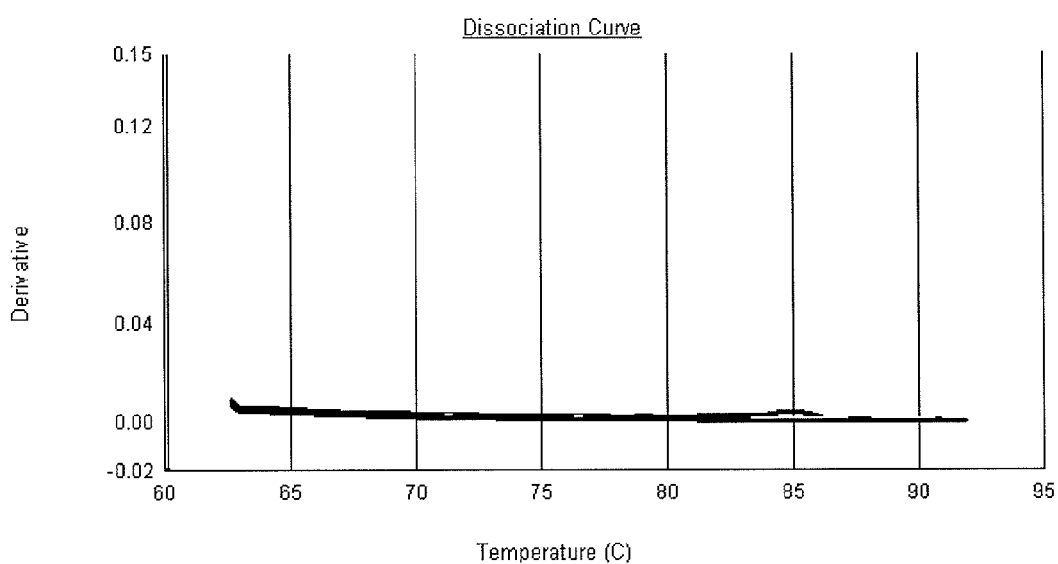
FIG. 2 shows a result of an analysis of melting curve obtained based on the results of the real-time PCR by the intercalator method using the Primer rpoB_2 and using plasmid DNA comprising wild type rpoB gene sequence as a template obtained in Example 1.

The real-time PCR was performed using each DNA sample as a template, and the melting curves which was made based on the obtained results were shown in FIG. 1 and FIG. 2.

FIG. 1 shows a result of the real-time PCR performed by using the Primer rpoB_2 of the present invention and using a plasmid DNA comprising mutant type rpoB gene sequence_2 as a template.

On the other hand, FIG. 2 shows a result of the real-time PCR performed by using the Primer rpoB_2 of the present invention and using a plasmid DNA comprising the wild type rpoB gene sequence as a template.

As is clear from FIG. 1, when the real-time PCR is performed by using the Primer rpoB_2 of the present invention and using a plasmid DNA comprising mutant type rpoB gene sequence_2 as a template, the amplification of DNA was confirmed. In addition, the peak positions, namely, the Tm value of the melting curve for each DNA sample with $10^5$, $10^4$, $10^3$ and $10^2$ copies were overlapped.

On the other hand, as is clear from FIG. 2, when the real-time PCR is performed in the same method using the Primer rpoB_2 of the present invention and using a plasmid DNA comprising wild type rpoB gene sequence as a template, the peak did not appear, and the primer extension product of the DNA was not obtained.

From the results described above, it is found that it becomes possible to eliminate completely any false positive result in the detection, and to detect only the target having a mutant sequence, namely, the DNA sample having a mutant sequence specifically and with high accuracy, by conducting the real-time PCR using a primer of the present invention which has a single base substitution at the 3'end thereof, and has a nucleotide with a modification capable of inhibiting the reaction of the nucleic acid synthesis at the second position from the 3'end thereof, Comparative Example 1

(1) Plasmid DNA Comprising the Mutant Type rpoB Gene Sequence

The "mutant type rpoB gene sequence_2" obtained in Example 1 (1) was used.

(2) Primer for the Detection of Mutant Type rpoB Gene (Construction of Primer rpoB_2_n3)

A primer having a nucleotide sequence shown in the same SEQ ID NO:7 as that for the Primer rpoB_2 obtained in Example 1 (2), while the $3^{rd}$ "C" from the 3'end thereof is modified with a nucleotide analog (2'-O,4'-C-Ethylene-bridged Nucleic Acids) and the second "C" from the 3' end thereof is not modified with 2'-O,4'-C-Ethylene-bridged Nucleic Acids, was designed. This primer is described as "Primer rpoB_2_n3".

The designed "Primer rpoB_2_n3" was obtained through the use of custom service of Sigma Genosys.

(3) Detection of the Mutant Type rpoB Gene by the Real-Time PCR Detection and Determination of the Effects from False Positive Reactions 1) Preparation of DNA Sample for PCR The same one as prepared in Example 1 (3) 1) (the dilution series of plasmid DNA comprising the mutant type rpoB gene sequence_2) was used.

2) Preparation of the Reaction Solution for PCR

A 10 mM Tris-HCl (pH 8.9) containing each 300 nM of the Primer rpoB_2_n3 obtained in the above-described (2), a universal primer (M13-forward primer, Takara Bio Inc.), a 30 times dilution (30000 times dilution in final) of the original concentration of SYBR™ Green I (trade name of Molecular Probes Inc.) as intercalating dye, 1.5 mM $MgCl_2$, 80 mM KCl, 500 μg/ml of BSA, 0.1% sodium cholate, 0.1% TritonX-100, 0.2 mM each of dATP, dCTP, dGTP and dTTP, and 40 U/ml of Taq DNA polymerase (produced by Nippon Gene Co., Ltd.) was prepared, and used the solution as a reaction solution for PCR.

3) Real-Time PCR

The real-time PCR was performed by the same method as described in Example 1 (3) 3) except for using the reaction solution for PCR prepared in the above-described (3) 2) as a reaction solution, and the fluorescent intensity emitted from SYBR™ Green I intercalating into the amplification products was measured.

In addition, using a plasmid DNA comprising the wild type rpoB gene sequence prepared in Example 1 (1) 2) as a DNA sample (template DNA), and by the same method except for the use of above-described plasmid DNA, the preparation of DNA sample, the preparation of the reaction solution and the real-time PCR were performed.

(4) Melting Curve Analysis

The melting curve was made for each amplification product for the dilution series of the DNA sample by plotting the melting temperature of amplification product (double-stranded DNA) as horizontal axis and the first derivation (variation) of fluorescent intensity as vertical axis, and detection of peak was examined.

(5) Results

Figure 3:
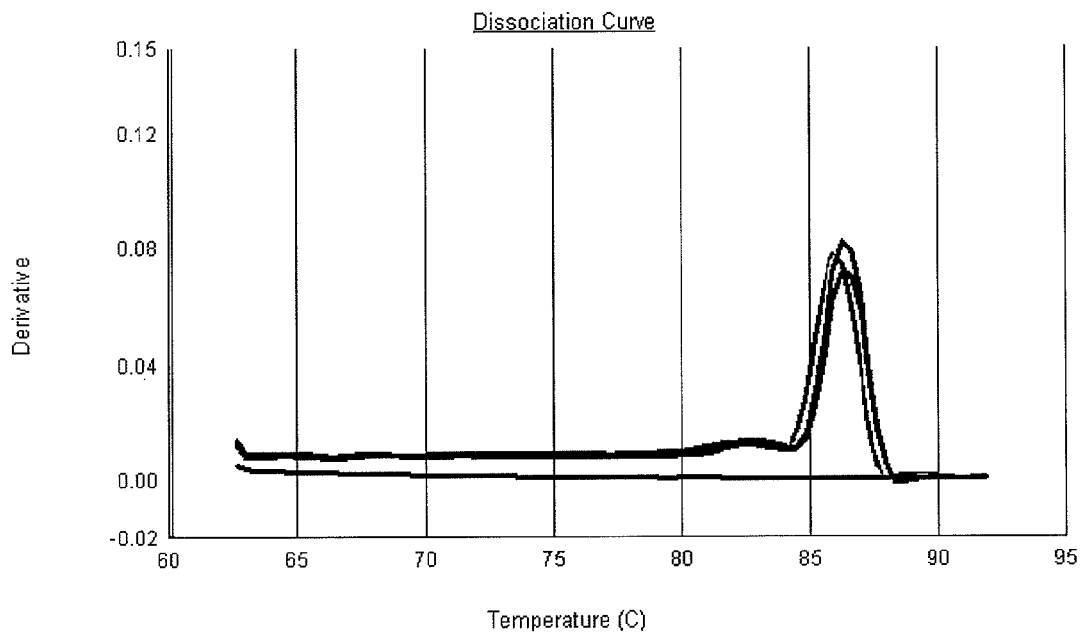
FIG. 3 shows a result of analysis of melting curve obtained based on the results of the real-time PCR by the intercalator method using the Primer rpoB_2_n3 and using plasmid DNA comprising mutant type rpoB gene sequence_2 as a template obtained in Comparative Example 1.
Figure 4:
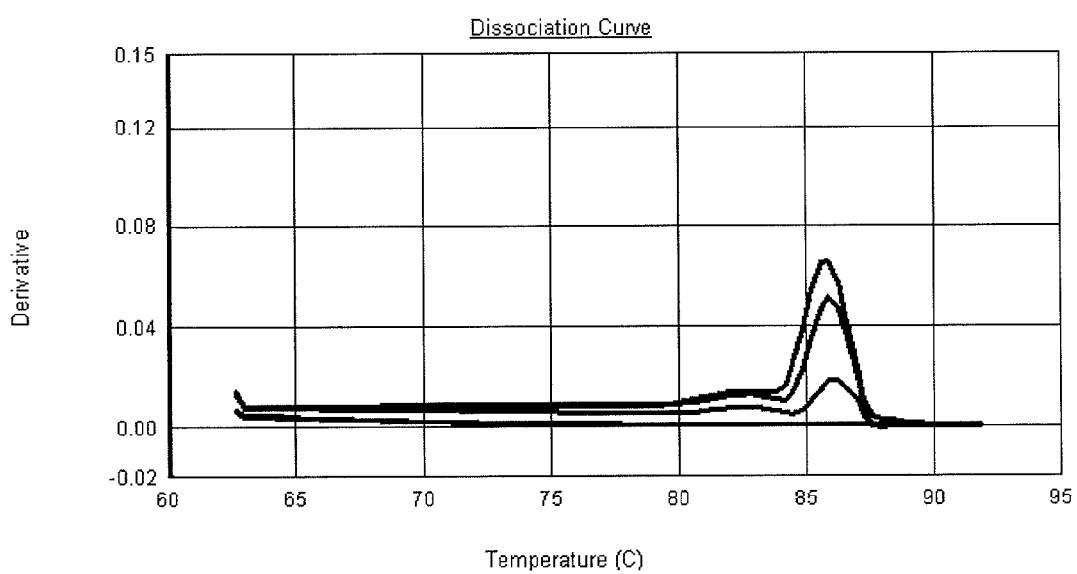
FIG. 4 shows a result of analysis of melting curve obtained based on the results of the real-time PCR by the intercalator method using the Primer rpoB_2_n3 and using plasmid DNA comprising wild type rpoB gene sequence_2 as a template obtained in Comparative Example 1.

The real-time PCR was performed using each DNA sample as a template, and the melting curves which was made based on the obtained results were shown in FIG. 3 and FIG. 4.

FIG. 3 shows a result of the real-time PCR performed by using the Primer rpoB_2_n3 and using a plasmid DNA comprising mutant type rpoB gene sequence_2 as a template.

On the other hand, FIG. 4 shows a result of the real-time PCR performed by using the Primer rpoB_2_n3 and using a plasmid DNA comprising the wild type rpoB gene sequence_2 as a template.

As is clear from FIG. 3, when the real-time PCR is performed by using the Primer rpoB_2_n3 and using a plasmid DNA comprising mutant type rpoB gene sequence_2 as a template, the amplification of DNA was confirmed.

However, as is clear from FIG. 4, when the real-time PCR is performed in the same method using the Primer rpoB_2_n3 and using a plasmid DNA comprising wild type rpoB gene sequence as a template, the amplification of DNA was also confirmed. That is, the peak of false positive amplification was confirmed.

From the results described above, it is found that when PCR is performed using an oligonucleotide wherein a nucleotide having a modification capable of inhibiting the reaction of nucleic acid synthesis is allocated at the $3^{rd}$ position from 3'end thereof as a template, the accurate determination of mutant type can not be made.

Example 2

Detection of Drug Resistant Tubercle Bacillus: Model Experiment 2

(1) Construction of Plasmid DNA Comprising Mutant Type rpoB gene Sequence_6

By the same method as Example 1 (1) 1), introduction of mutation into a base at the $68^{th}$ from the 5'end of the sequence of a hot spot mutation region in rpoB gene to "C" was performed, while it should be "T" in the wild type.

The mutation-introduced DNA fragment was purified using a column produced by QIAGEN K.K., and then inserted into a cloning vector (produced by Invitrogen Corporation). After that, using QIAprep™ Spin Miniprep Kit (produced by QIAGEN K.K.), the plasmid DNA comprising objective sequence was purified and recovered.

The plasmid DNA obtained by the above-described method comprises a nucleotide sequence shown in SEQ ID NO:4 described below. This nucleotide sequence shown in SEQ ID NO:4 is hereinafter described as "mutant type rpoB gene sequence_6". In the sequence of "the mutant type rpoB gene sequence_6", the underlined base at the $86^{th}$ from the 5' end thereof corresponds to the base at the $68^{th}$ from the 5' end in a hot spot mutation region in rpo B gene. And, a base at this position in the wild type rpo B gene is "T", but is substituted into "C" in the "mutant type rpoB gene sequence_6".

```
SEQ ID NO:4:
5'-TTCTTCGGCACCAGCCAGCTGAGCCAATTCATGGACCAGAACAACCC

GCTGTCGGGGTTGACCTACAAGCGCCGACTGTCGGCGCCGGGG-3'

(mutant type rpoB gene sequence_6)
```

(2) Construction of a Primer (Primer rpoB_6) for Detecting Mutant Type rpoB Gene Based on the mutant type rpoB gene sequence_6, primer was designed by the following method.

First, the primer sequence for the detection of the mutant type rpoB gene was designed so that (i) the position to be introduced with a mutation in the mutant type rpoB gene sequence 6, namely, the base "C" at the 86$^{th}$ from the 5' end thereof, will be set at the 3'end of the primer, (ii) the other sequence of the primer will be set to be identical to the nucleotide sequence with 14 bases toward 5'-side from the base "C" at the 86$^{th}$ from the 5' end of the mutant type rpoB gene sequence 6 and moreover (iii) the base "C" at the second position from the 3' end of the primer will be substituted with the "C" which is modified with 2'-O,4'-C-Ethylene-bridged Nucleic Acids. The oligonucleotide designed in this method is described as "Primer rpoB_6". The nucleotide sequence of "Primer rpoB_6" is shown in the following SEQ ID NO:8.

That is, in the nucleotide sequence shown in SEQ ID NO:8 described below, the underlined nucleotide at the 3' end is the position where the "T" in the wild type is substituted into "C". In addition, the base "C" at the second position from the 3' end is the "C" which is modified with 2'-O,4'-C-Ethylene-bridged Nucleic Acids.

```
SEQ ID NO:8: 5'-CCGACTGTCGGCGCC-3'
```

The designed "Primer rpoB_6" was obtained through the use of custom service of Sigma Genosys.

(3) Detection of the Mutant Type rpoB Gene by the Real-Time PCR Detection and Determination of the Effects from False Positive Reactions 1) Preparation of DNA Sample for PCR By measuring absorbance of the plasmid DNA sample comprising the mutant type rpoB gene sequence_6 obtained in the above-described (1), the amount of DNA in the plasmid DNA sample was measured. In the next place, the plasmid DNA sample was diluted using 10 mM Tris-HCl buffer (pH 8.9) to prepare a dilution series of $10^5$, $10^4$, $10^3$, and $10^2$ copies/μl, and used as DNA samples for PCR.

2) Preparation of the Reaction Solution for PCR

A 10 mM Tris-HCl (pH 8.9) containing each 300 nM of the Primer rpoB_6 obtained in the above-described (2) and a universal primer (M13-forward primer, Takara Bio Inc.), a 30 times dilution (30000 times dilution in final) of the original concentration of SYBR™ Green I (trade name of Molecular Probes Inc.) as intercalating dye, 1.5 mM $MgCl_2$, 80 mM KCl, 500 μg/ml of BSA, 0.1% sodium cholate, 0.1% TritonX-100, 0.2 mM each of dATP, dCTP, dGTP and dTTP, and 40 U/ml of Taq DNA polymerase (produced by Nippon Gene Co., Ltd.) was prepared, and used as a reaction solution for PCR.

3) Real-Time PCR

Using a plasmid DNA comprising the mutant type rpoB gene sequence_6 prepared in the above-described (1) as a template DNA (an amplification target), real-time PCR was performed. In addition, by the method described below, the quantitative monitoring by intercalation method was performed, and the result of real-time PCR were studied and evaluated.

That is, 1 μl of each dilution series of the DNA sample for PCR prepared in the above-described (3) 1) and 19 μl of the reaction solution for PCR prepared in the above-described (3) 2) were placed in a well of a 96-well reaction plate (Micro-Amp Optical 96-Well Reaction Plate, produced by Applied Biosystems Japan), and the real-time PCR was performed by using personal thermal cycler and detection system for Taq-Man™ PCR (ABI 7500, produced by Applied Biosystems Japan). Namely, after the reaction solution was heated at 95° C. for 10 minutes, a reaction cycle consisting a reaction at 95° C. for 15 seconds and a reaction at 60° C. for 1 minute was repeated for 40 cycles. After that, the fluorescent intensity emitted from SYBR™ Green I intercalated into the amplification products was measured.

In addition, by the same method as described in Example 2 (3) except for the use of the plasmid DNA comprising the wild type rpoB gene sequence prepared in Example 1 (1) 2) as a template DNA, the preparation of DNA sample for PCR, preparation of the reaction solution for PCR and the real-time PCR were performed.

(4) Melting Curve Analysis

The melting curve was made for each amplification product for the dilution series of the DNA sample for PCR by plotting the melting temperature of amplification product (double-stranded DNA) as horizontal axis and the first derivation (variation) of fluorescent intensity as vertical axis, and detection of peak was examined.

(5) Results

Figure 5:
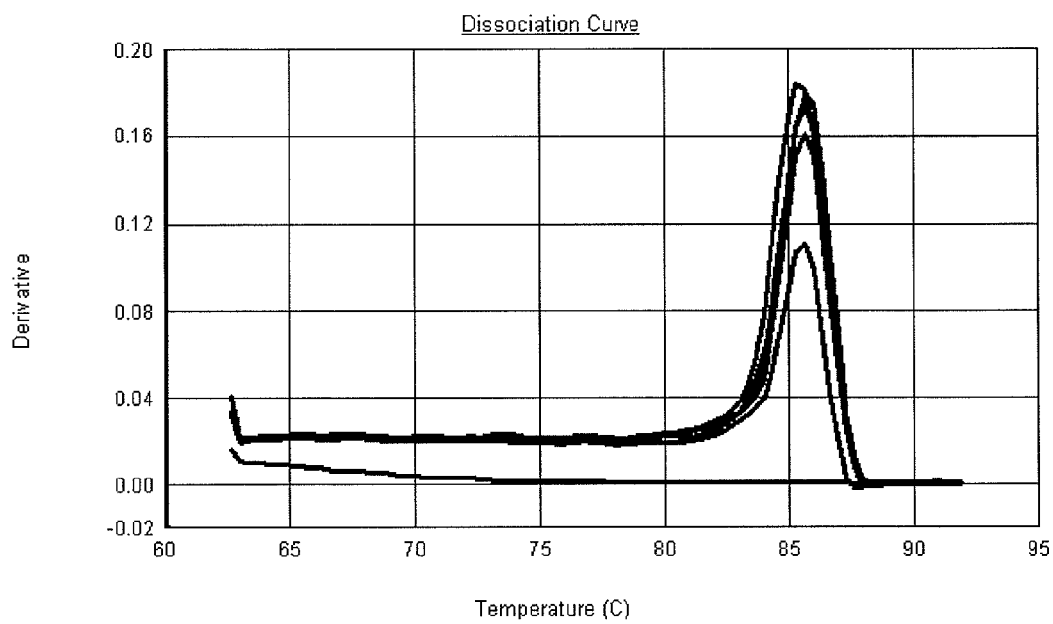
FIG. 5 shows a result of analysis of melting curve obtained based on the results of the real-time PCR by the intercalator method using a Primer rpoB_6 and using plasmid DNA comprising mutant type rpoB gene sequence_6 as a template obtained in Example 2.
Figure 6:
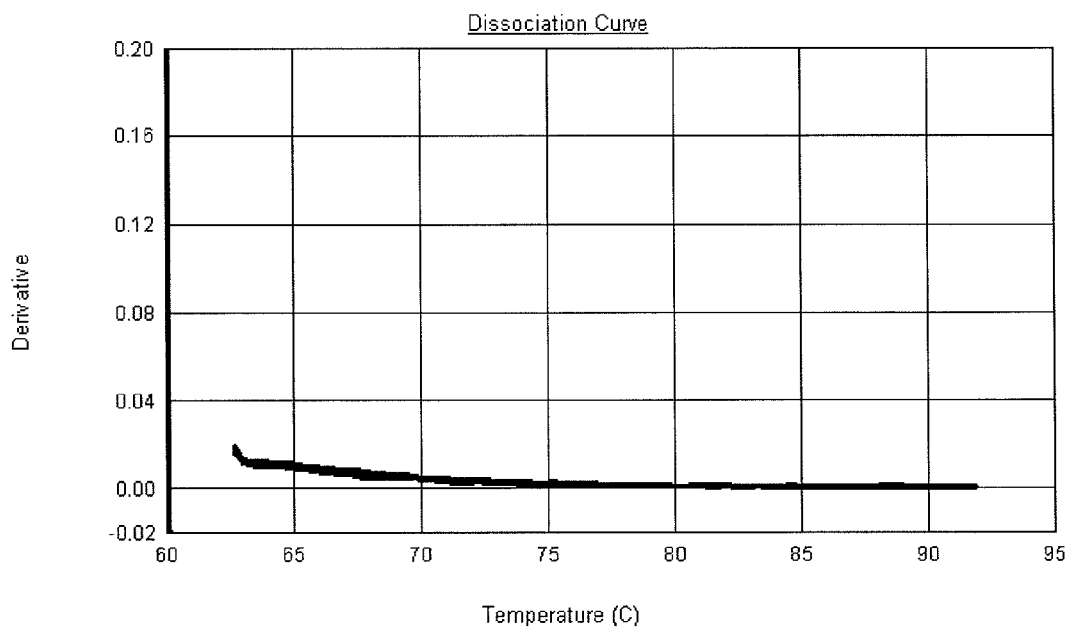
FIG. 6 shows a result of analysis of melting curve obtained based on the results of the real-time PCR by the intercalator method using a Primer rpoB_6 and using plasmid DNA comprising wild type rpoB gene sequence as a template obtained in Example 2.

The real-time PCR was performed by using each DNA sample as a template, and the melting curves which was made based on the obtained results were shown in FIG. 5 and FIG. 6.

FIG. 5 shows a result of the real-time PCR performed by using the Primer rpoB_6 of the present invention, and using a plasmid DNA comprising mutant type rpoB gene sequence_6 as a template.

On the other hand, FIG. 6 shows a result of the real-time PCR performed by using the Primer rpoB_6 of the present invention and a plasmid DNA comprising the wild type rpoB gene sequence as a template.

As is clear from FIG. 5, when the real-time PCR is performed by using the Primer rpoB_6 of the present invention and using a plasmid DNA comprising mutant type rpoB gene sequence_6 as a template, the amplification of DNA was confirmed. In addition, the peak position of the melting curve for each DNA sample with $10^5$, $10^4$, $10^3$ and $10^2$ copies were overlapped. Namely, the Tm value was consistent.

On the other hand, as is clear from FIG. 6, when the real-time PCR is performed using the Primer rpoB_6 of the present invention and using a plasmid DNA comprising wild type rpoB gene sequence as a template, the peak did not appear, and the primer extension product of the DNA was not obtained.

From the results described above, it is found that, any false positive result in the detection can be eliminated completely and only the target having a mutant sequence can be detected specifically and with high accuracy, by conducting the real-time PCR by using a primer of the present invention which has a single base substitution at the 3' end thereof, and has a nucleotide with a modification capable of inhibiting the reaction of nucleic acid synthesis allocated at the second position from the 3' end thereof.

Example 3

Simultaneous Detection of Plural Mutant Gene (1) Construction of Plasmid DNA Comprising Mutant Type rpoB Gene Sequence
1) Construction of Plasmid DNA Comprising Mutant Type rpoB gene Sequence_3

By the same method as Example 1 (1) 1), introduction of mutation into a base at the 46$^{th}$ from the 5'end of the sequence of a hot spot mutation region in rpoB gene to "G" was performed, while it should be "C" in the wild type.

The mutation-introduced DNA fragment was purified using a column produced by QIAGEN K.K., and then inserted into a cloning vector (produced by Invitrogen Corporation). After that, using QIAprep™ Spin Miniprep Kit (produced by QIAGEN K.K.), the plasmid DNA comprising objective sequence was purified and recovered.

The plasmid DNA obtained by the above-described method comprises a nucleotide sequence shown in SEQ ID NO:5 below. This nucleotide sequence shown in SEQ ID NO:5 is hereinafter described as "mutant type rpoB gene sequence_3". In the sequence of the "mutant type rpoB gene sequence_3", the underlined base at the 64$^{th}$ from the 5'end thereof corresponds to the base at the 46$^{th}$ from the 5'end in a hot spot mutation region in rpo B gene. And, a base at this position in the wild type rpo B gene is "C", but is substituted into "G" in the "mutant type rpoB gene sequence_3".

SEQ ID NO:5:
5'-TTCTTCGGCACCAGCCAGCTGAGCCAATTCATGGACCAGAACAACCC

GCTGTCGGGGTTGACCGACAAGCGCCGACTGTCGGCGCTGGGG-3'

(mutant type rpoB gene sequence_3)

2) Construction of Plasmid DNA Comprising Mutant Type rpoB Gene Sequence_4

By the same method as Example 1 (1) 1), introduction of mutation into a base at the 47$^{th}$ from the 5'end of the sequence of a hot spot mutation region in rpoB gene to "T" was performed, while it should be "A" in the wild type.

The mutation-introduced DNA fragment was purified using a column produced by QIAGEN K.K., and then inserted into a cloning vector (produced by Invitrogen Corporation). After that, using QIAprep™ Spin Miniprep Kit (produced by QIAGEN K.K.), the plasmid DNA comprising objective sequence was purified and recovered.

The plasmid DNA obtained by the above-described method comprises a nucleotide sequence shown in SEQ ID NO:6 described below. This nucleotide sequence shown in SEQ ID NO:6 is hereinafter described as "mutant type rpoB gene sequence_4". In the sequence of the "mutant type rpoB gene sequence_4", the underlined base at the 65$^{th}$ from the 5'end thereof corresponds to the base at the 47$^{th}$ from the 5'end in a hot spot mutation region in rpo B gene. And, a base at this position in the wild type rpo B gene is "A", but is substituted into "T" in the "mutant type rpoB gene sequence_4".

SEQ ID NO:6:
5'-TTCTTCGGCACCAGCCAGCTGAGCCAATTCATGGACCAGAACAACCC

GCTGTCGGGGTTGACCCTCAAGCGCCGACTGTCGGCGCTGGGG-3'

(mutant type rpoB gene sequence_4)

rpoB gene sequence 4)
(2) Construction of a Primer for Detection of Mutant Type rpoB Gene
1) Construction of "Primer rpoB_3"

Based on the mutant type rpoB gene sequence_3, the primer was designed by the following method.

First, the primer sequence for the detection of the mutant type rpoB gene was designed so that (i) the position to be introduced with a mutation in the mutant type rpoB gene sequence 3, namely, the base "G" at the 64$^{th}$ from the 5' end thereof, will be set the 3' end of the primer, (ii) the other sequence of the primer will be set to be identical to the nucleotide sequence with 16 bases toward 5'-side from the base "G" at the 64$^{th}$ from the 5' end in the mutant type rpoB gene sequence_3, and moreover (iii) the base "C" at the second position from the 3' end of the primer will be substituted with the "C" which is modified with 2'-O,4'-C-Ethylene-bridged Nucleic Acids. The oligonucleotide designed in this method is described as "Primer rpoB_3". The nucleotide sequence of the "Primer rpoB_3" is shown in the following SEQ ID NO:9.

That is, in the nucleotide sequence shown in the SEQ ID NO:9 described below, the underlined nucleotide at the 3'end is the position where the "C" in the wild type is substituted into "G". In addition, the base "C" at the second position from the 3'end is the "C" which is modified with 2'-O,4'-C-Ethylene-bridged Nucleic Acids.

SEQ ID NO:9: 5'-GCTGTCGGGGTTGACCG-3'

The designed "Primer rpoB_3" was obtained through the use of custom service of Sigma Genosys.

2) Construction of "Primer rpoB_4"

Based on the mutant type rpoB gene sequence_4 the primer was designed by the following method.

First, the primer sequence for the detecting the mutant type rpoB gene was designed so that (i) the position to be introduced with a mutation in the mutant type rpoB gene sequence_4, namely, the base "T" at the 47$^{th}$ from the 5'end thereof, will be set at the 3'end of the primer, (ii) the other sequence of the primer will be set to be identical to the nucleotide sequence with 16 bases toward the 5'-side from the base "T" at the 47$^{th}$ from the 5'end in the mutant type rpoB gene sequence_4 and moreover (iii) the base "C" at the second position from the 3'end of the primer will be substituted with the "C" which is modified with 2'-O,4'-C-Ethylene-bridged Nucleic Acids. The oligonucleotide designed in this method is described as "Primer rpoB_4". The nucleotide sequence of the "Primer rpoB_4" is shown in the following SEQ ID NO:10.

That is, in the nucleotide sequence shown in the SEQ ID NO: 10 described below, the underlined nucleotide at the 3'end is the position where the "A" in the wild type is substituted into "T". In addition, the base "C" at the second position from the 3'end is the "C" which is modified with 2'-O,4'-C-Ethylene-bridged Nucleic Acids.

SEQ ID NO:10: 5'-CTGTCGGGGTTGACCCT-3'

The designed "Primer rpoB_4" was obtained through the use of custom service of Sigma Genosys.

(3) Detection of the Mutant Type rpoB Gene by the Real-Time PCR Detection and Determination of the Effects from False Positive Reactions
1) Preparation of DNA Sample for PCR By measuring absorbance of the plasmid DNA sample comprising the mutant type rpoB gene sequence_3 obtained in the above-described (1) 1) and the plasmid DNA sample comprising the mutant type rpoB gene sequence_4 obtained in the above-described (1) 2), the amount of DNA in each plasmid DNA samples was measured.

In the next place, the plasmid DNA samples comprising the mutant type rpoB gene sequence_2 obtained in Example I (1) 1), the mutant type rpoB gene sequence_3 obtained in the above-described (1) 1) and the mutant type rpoB gene sequence_4 obtained in the above-described (1) 2) were each diluted using 10 mM Tris-HCl buffer (pH 8.9) to prepare each dilution series of $10^5$, $10^4$, $10^3$, and $10^2$ copies/μl, and each were used as DNA samples for PCR.

2) Preparation of the Reaction Solution for PCR

A 10 mM Tris-HCl (pH 8.9) containing each 300 nM of the Primer rpoB_2 obtained in (2) of Example 1, the Primer rpoB_3 and the Primer rpoB_4 obtained in the above-described (2), a universal primer (M13-forward primer, Takara Bio Inc.), a 30 times dilution (30000 times dilution in final) of the original concentration of SYBR™ Green I (trade name of Molecular Probes Inc.) as intercalating dye, 1.5 mM $MgCl_2$, 80 mM KCl, 500 μg/ml of BSA, 0.1% sodium cholate, 0.1% TritonX-100, 0.2 mM each of dATP, dCTP, dGTP and dTTP, and 40 U/ml of Taq DNA polymerase (produced by Nippon Gene Co., Ltd.) was prepared, and used as a reaction solution for PCR. That is, in this reaction solution, three kinds of primers, the Primer rpoB_2, the Primer rpoB_3 and the Primer rpoB_4 are contained for the detection of mutant type rpoB gene.

3) Real-Time PCR

Using the plasmid DNA samples comprising the mutant type rpoB gene sequence_2 obtained in Example 1 (1) 1), the mutant type rpoB gene sequence_3 obtained in the above-described (1) 1), or the mutant type rpoB gene sequence_4 obtained in the above-described (1) 2) as a template DNA (an amplification target), real-time PCR was performed. In addition, by the method described below, the quantitative monitoring by intercalation method was performed, and the results of real-time PCR were studied and evaluated.

That is, 1 μl of each dilution series of the DNA sample for PCR prepared in the above-described (3) 1) and 19 μl of the reaction solution for PCR prepared in the above-described (3) 2) were placed in a well of a 96-well reaction plate (Micro-Amp Optical 96-Well Reaction Plate, produced by Applied Biosystems Japan), and the real-time PCR was performed by using personal thermal cycler and detection system for Taq-Man™ PCR (ABI 7500, produced by Applied Biosystems Japan). Namely, after the reaction solution was heated at 95° C. for 10 minutes, a reaction cycle consisting of a reaction at 95° C. for 15 seconds and a reaction at 60° C. for 1 minute was repeated for 40 cycles. After that, the fluorescent intensity emitted from SYBR™ Green I intercalated into the amplification products was measured.

(4) Melting Curve Analysis

The melting curve was made for each amplification product for the dilution series of each DNA sample for PCR by plotting the melting temperature of amplification product (double-stranded DNA) as horizontal axis and the first derivation (variation) of fluorescent intensity as vertical axis, and detection of peak was examined.

(5) Results

Figure 7:
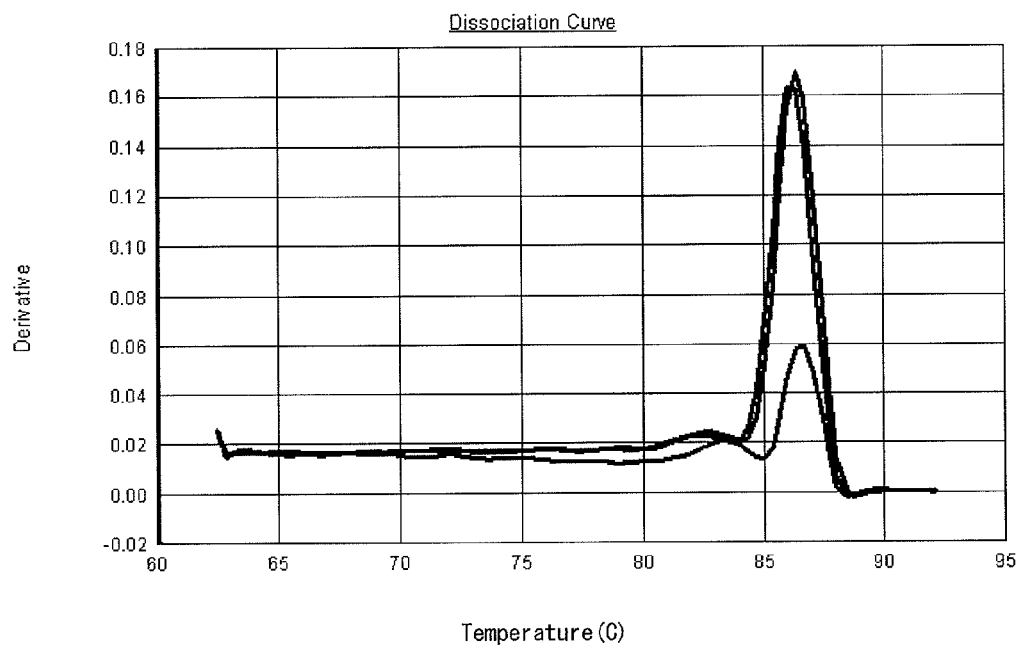
FIG. 7 shows a result of analysis of melting curve obtained based on the results of the real-time PCR by the intercalator method using a mixed primer of Primer rpoB_2, Primer rpoB_3 and Primer rpoB_4 and using plasmid DNA comprising mutant type rpoB gene sequence_2 as a template obtained in Example 3.
Figure 8:
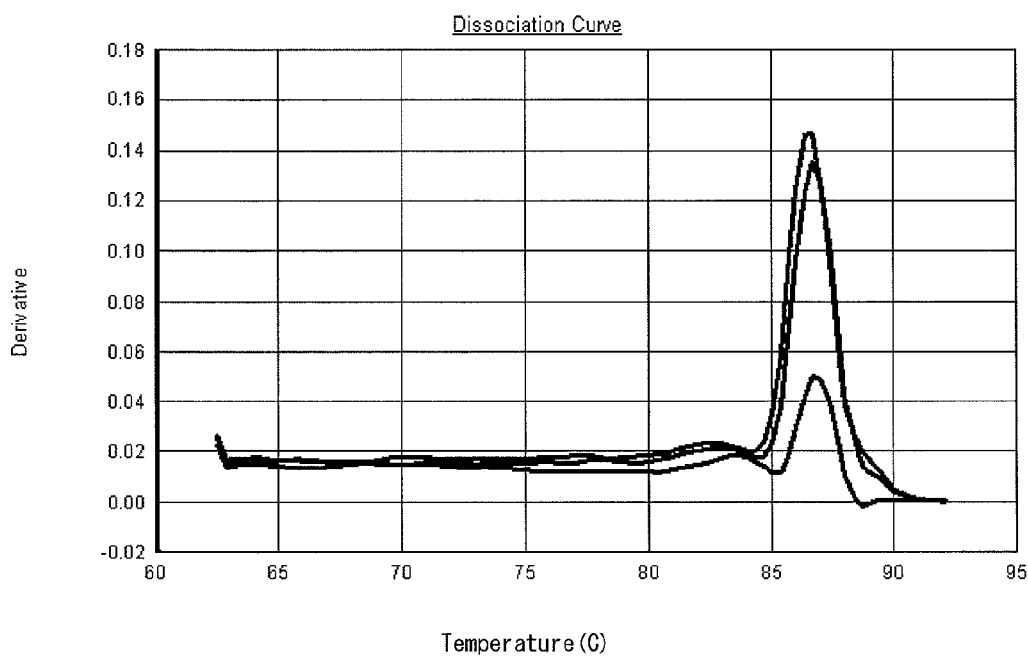
FIG. 8 shows a result of analysis of melting curve obtained based on the results of the real-time PCR by the intercalator method using a mixed primer of Primer rpoB_2, Primer rpoB_3 and Primer rpoB_4 and using plasmid DNA comprising mutant type rpoB gene sequence_3 as a template obtained in Example 3.
Figure 9:
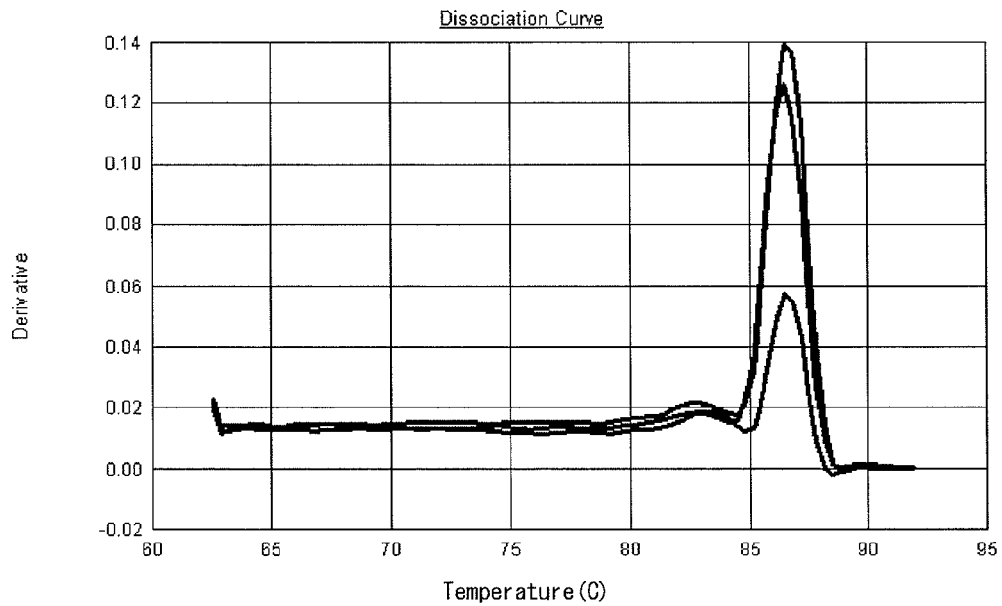
FIG. 9 shows a result of analysis of melting curve obtained based on the results of the real-time PCR by the intercalator method using a mixed primer of Primer rpoB_2, Primer rpoB_3 and Primer rpoB_4 and using plasmid DNA comprising mutant type rpoB gene sequence_4 as a template obtained in Example 3.

Using each DNA sample as a template, and using a mixed primer comprising Primer rpoB_2, Primer rpoB_3 and Primer rpoB_4, the real-time PCR was performed, and the melting curves was made based on the obtained results were shown in FIG. 7 to FIG. 9.

FIG. 7 shows a result of the real-time PCR using a plasmid DNA comprising mutant type rpoB gene sequence_2 as a template.

FIG. 8 shows a result of the real-time PCR using a plasmid DNA comprising mutant type rpoB gene sequence_3 as a template.

FIG. 9 shows a result of the real-time PCR using a plasmid DNA comprising mutant type rpoB gene sequence_4 as a template.

Comparative Example 2

By the same method as described in Example 3 (3) except for the use of a plasmid DNA comprising the wild type rpoB gene sequence obtained in Example 1 (1) 2) as a template DNA, preparation of DNA sample for PCR, preparation of reaction solution for PCR, and the real-time PCR was performed by using the Primer rpoB_2, the Primer rpoB_3, the Primer rpoB_4 and M-13 forward primer, and then the fluorescent intensity emitted from SYBR™ Green I intercalated into the amplification products was measured.

In the next place, the melting curve was made for each amplification product for the dilution series of each DNA sample for PCR by plotting the melting temperature of amplification product (double-stranded DNA) as horizontal axis and the first derivation (variation) of fluorescent intensity as vertical axis, and detection of peak was examined.

Figure 10:
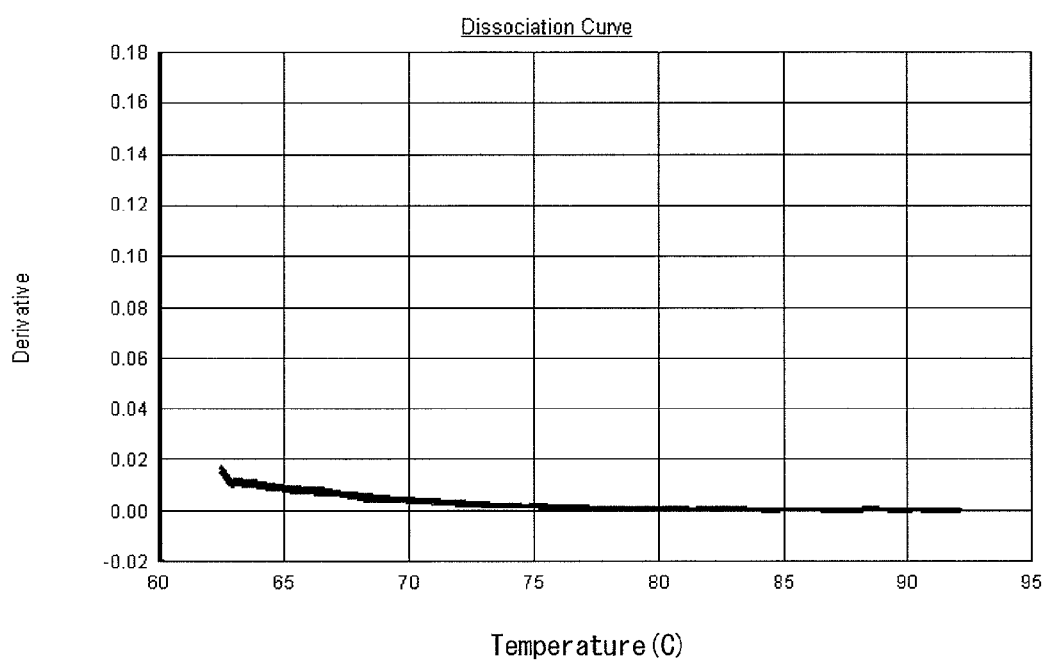
FIG. 10 shows a result of analysis of melting curve obtained based on the results of the real-time PCR by the intercalator method using a mixed primer of Primer rpoB_2, Primer rpoB_3 and Primer rpoB_4 and using plasmid DNA comprising wild type rpoB gene sequence as a template obtained in Comparative Example 2.

The real-time PCR was performed using each DNA sample as a template, and the melting curves made based on the obtained results were shown in FIG. 10.

As is clear from FIG. 10, when the real-time PCR is performed using several kinds of primers of the present invention and using a plasmid DNA comprising wild type sequence as a template, the peak of the primer extension product did not appear. On the other hand, as is clear from FIG. 7 to 9, when the real-time PCR is performed using several kinds of primers of the present invention and using a plasmid DNA comprising mutant type rpoB gene sequence_2, mutant type rpoB gene sequence_3 or mutant type rpoB gene sequence_4 as a template, the primer extension product was obtained in each case. That is, by using three kinds of primers of the present invention at the same time, three kinds of mutant gene can be detected.

From the results described above, it is found that, even when the real-time PCR is performed using plural primers of the present invention, it is possible to eliminate completely any false positive result in the detection, and moreover, as single run of PCR can deal with various types of mutation pattern, it is possible to establish a determination system for drug resistance by multiplex PCR.

Industrial Applicability

For example, for the microbial sensitivity test which is an examination on drug resistance property of bacteria and accepted as an essential test in diagnosis (treatment) of tuberculosis, through the use of in-Line separate detection (On chip PCR system) as a genetic test item, and in combination with the genetic diagnosis of tubercle bacillus and nontuberculous acid-fast bacterium disease, it becomes possible to perform the determination of drug-resistance in a single tube (1 line).

Particularly, according to the present invention, it becomes possible to completely eliminate any false positive result in the determination and to deal with various mutation patterns in a single run of PCR reaction. Therefore, it becomes possible to construct a drug-resistance determination system, which can detect any possible genetic mutation by a single run of multiplex PCR.

What is claimed is:

1. A method for detecting mutation(s) in a nucleotide sequence comprising:
performing a nucleic acid amplification reaction in the presence of DNA polymerase having exonuclease activity by using any one of the following oligonucleotides (a) to (d) or a salt thereof as a primer, using a probe labeled with a reporter fluorescent dye and a quencher dye, a dye labeled probe, or an intercalator, and using a nucleic acid in a sample as a template, and detecting a reaction product in real time;
(a) an oligonucleotide,
  i) wherein the oligonucleotide has the same nucleotide as a mutant nucleotide in a target gene at the 3' end position thereof,
  ii) wherein the oligonucleotide has the same nucleotide sequence as a nucleotide sequence of the target gene except for its 3' end position, and has the same nucleotide sequence as the nucleotide sequence of the target gene toward the 5'-side from the position where the mutant nucleotide may exist in the target gene, and
  iii) wherein the nucleotide at the second position from the 3' end thereof has a modification that inhibits a reaction of nucleic acid synthesis,
or a salt thereof;
(b) an oligonucleotide,
  i) wherein the oligonucleotide has a nucleotide complementary to a mutant nucleotide in a target gene at the 3' end position thereof,
  ii) wherein the oligonucleotide has a nucleotide sequence complementary to a nucleotide sequence of the target gene except for its 3' end position, and has a nucleotide sequence complementary to the nucleotide sequence of the target gene toward the 3'-side from a position where the mutant nucleotide may exist in the target gene, and
  iii) wherein the nucleotide at the second position from the 3' end thereof has a modification that inhibits a reaction of nucleic acid synthesis,
or a salt thereof;
(c) an oligonucleotide,
  i) wherein the oligonucleotide has the same nucleotide as a reference nucleotide in a target gene at the 3' end position thereof,
  ii) wherein the oligonucleotide has the same sequence as a nucleotide sequence of the target gene except for its 3' end position, and has the same nucleotide sequence as the nucleotide sequence of the target gene toward the 5'-side from a position where the reference nucleotide exist in the target gene, and
  iii) wherein the nucleotide at the second position from the 3' end thereof has a modification that inhibits a reaction of nucleic acid synthesis,
or a salt thereof;
(d) an oligonucleotide,
  i) wherein the oligonucleotide has a nucleotide complementary to a reference nucleotide in a target gene at the 3' end position thereof,
  ii) wherein the oligonucleotide has a nucleotide sequence complementary to a nucleotide sequence of the target gene except for its 3' end position, and has a nucleotide sequence complementary to the nucleotide sequence of the target gene toward the 3'-side from a position where the reference nucleotide exist in the target gene, and
  iii) wherein the nucleotide at the second position from the 3' end thereof has a modification that inhibits a reaction of nucleic acid synthesis,
or a salt thereof,
wherein the nucleotide having a modification that inhibits the reaction of nucleic acid synthesis is represented by formula [I] or [II],

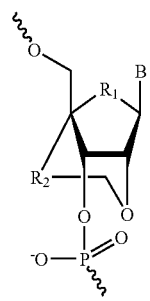

wherein B represents a nucleic acid base; $R_1$ represents an oxygen atom, a —NH group, or a lower alkylene group; and $R_2$ represents a lower alkylene group;

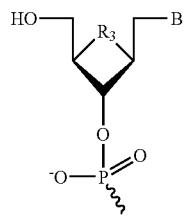

wherein B represents a nucleic acid base; and $R_3$ represents an oxygen atom, a nitrogen atom, a —NH group, or a lower alkylene group, and wherein no reaction products are obtained if the 3' end nucleotide of the oligonucleotide is cleaved as a result of the exonuclease activity of the DNA polymerase and the nucleotide having the modification which inhibits a reaction of nucleic acid synthesis at the second position from the 3' end of the oligonucleotide becomes the 3' end nucleotide of the oligonucleotide.

2. The method according to claim 1, wherein the method further comprises an oligonucleotide as a primer capable of amplifying a sequence of interest by the nucleic acid amplification reaction in pairs with the oligonucleotide to be used as the primer in claim 1.

3. The method according to claim 1, wherein the primer comprises 15 to 30 bases.

4. The method according to claim 2, wherein the combination of primers comprising "an oligonucleotide or a salt thereof having the same nucleotide as a mutant nucleotide in a target gene at the 3' end position thereof; having the same nucleotide sequence as a nucleotide sequence of the target gene except for its 3' end position, and having the same nucleotide sequence as the nucleotide sequence of the target gene toward the 5'-side from the position where the mutant nucleotide may exist in the target gene; and further having a modification that inhibits a reaction of nucleic acid synthesis at the nucleotide at the second position from 3' end thereof", and "an oligonucleotide capable of amplifying a sequence of interest by the nucleic acid amplification reaction in pairs with the oligonucleotide" is such a combination that when the nucleic acid amplification reaction is performed with the nucleic acid in the sample as a template, the objective reaction product is obtained if the nucleic acid in the sample is mutant type, and the objective reaction products is not obtained if the nucleic acid in the sample is wild type, and wherein the detection is performed by detecting the mutant type of nucleic acid specifically by using the combination of primers.

5. The method according to claim 1, wherein the mutation(s) in nucleotide sequence is a genetic polymorphism.

6. The method according to claim 5, wherein the genetic polymorphism is due to a single base substitution, a single base deletion or a single base insertion.

7. The method according to claim 1, wherein the nucleotide having a modification that inhibits the reaction of nucleic acid synthesis is a nucleotide modified with 2'-O,4'-C-Ethylene-bridged Nucleic Acids (ENA).

8. The method according to claim 1, wherein the nucleic acid amplification reaction is polymerase chain reaction (PCR).

9. The method according to claim 5, wherein the genetic polymorphism is due to substitution, deletion, or insertion.

10. The method according to claim 2, wherein the primer comprises 15 to 30 bases.

11. The method according to claim 1, wherein the detection of the reaction product is performed using an intercalator method.

12. The method according to claim 8, further comprising the use of a probe labeled with a reporter fluorescent dye and a quencher dye.

* * * * *

SEQUENCE LISTING

<160> NUMBER OF SEQ ID NOS: 10

<210> SEQ ID NO 1
<211> LENGTH: 72
<212> TYPE: DNA
<213> ORGANISM: Mycobacterium tuberculosis

<400> SEQUENCE: 1
ctgagccaat tcatggacca gaacaacccg ctgtcggggt tgacccacaa gcgccgactg    60
tcggcgctgg gg                                                        72

<210> SEQ ID NO 2
<211> LENGTH: 90
<212> TYPE: DNA
<213> ORGANISM: Mycobacterium tuberculosis

<400> SEQUENCE: 2
ttcttcggca ccagccagct gagccaattc atggaccaga caacccgct gtcggggttg     60 acccacaagc gccgactgtc ggcgctgggg                                     90

<210> SEQ ID NO 3
<211> LENGTH: 90
<212> TYPE: DNA
<213> ORGANISM: Mycobacterium tuberculosis
<220> FEATURE:
<221> NAME/KEY: rpoB
<222> LOCATION: (64)..(64)
<223> OTHER INFORMATION: mutation
<220> FEATURE:
<221> NAME/KEY: mutation
<222> LOCATION: (64)..(64)
<223> OTHER INFORMATION: rpoB

<400> SEQUENCE: 3
ttcttcggca ccagccagct gagccaattc atggaccaga caacccgct gtcggggttg     60 acctacaagc gccgactgtc ggcgctgggg                                     90

<210> SEQ ID NO 4
<211> LENGTH: 90
<212> TYPE: DNA
<213> ORGANISM: Mycobacterium tuberculosis
<220> FEATURE:
<221> NAME/KEY: mutation
<222> LOCATION: (86)..(86)
<223> OTHER INFORMATION: rpoB

<400> SEQUENCE: 4
ttcttcggca ccagccagct gagccaattc atggaccaga acaacccgct gtcggggttg 60
acctacaagc gccgactgtc ggcgccgggg 90

<210> SEQ ID NO 5
<211> LENGTH: 90
<212> TYPE: DNA
<213> ORGANISM: Mycobacterium tuberculosis
<220> FEATURE:
<221> NAME/KEY: mutation

```
<222> LOCATION: (64)..(64)
<223> OTHER INFORMATION: rpoB

<400> SEQUENCE: 5
ttcttcggca ccagccagct gagccaattc atggaccaga acaacccgct gtcggggttg      60
accgacaagc gccgactgtc ggcgctgggg                                       90

<210> SEQ ID NO 6
<211> LENGTH: 90
<212> TYPE: DNA
<213> ORGANISM: Mycobacterium tuberculosis
<220> FEATURE:
<221> NAME/KEY: mutation
<222> LOCATION: (65)..(65)
<223> OTHER INFORMATION: rpoB

<400> SEQUENCE: 6
ttcttcggca ccagccagct gagccaattc atggaccaga acaacccgct gtcggggttg      60
accctcaagc gccgactgtc ggcgctgggg                                       90

<210> SEQ ID NO 7
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 7
gctgtcgggg ttgacct                                                     17

<210> SEQ ID NO 8
<211> LENGTH: 15
<212> TYPE: DNA
<213> ORGANISM: Artificial Sequence
<220> FEATURE:
<223> OTHER INFORMATION: Oligonucleotide Primer

<400> SEQUENCE: 8
ccgactgtcg gcgcc                                                       15

<210> SEQ ID NO 9
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 9
gctgtcgggg ttgaccg                                                     17

<210> SEQ ID NO 10
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 10
ctgtcggggt tgaccct                                                     17
```